United States Patent
Mizuoka et al.

(10) Patent No.: US 9,316,649 B2
(45) Date of Patent: Apr. 19, 2016

(54) BIOLOGICAL SAMPLE MEASURING DEVICE AND METHOD FOR MEASURING BIOLOGICAL SAMPLE USING SAME

(75) Inventors: Daiki Mizuoka, Ehime (JP); Hiroyuki Tokunaga, Ehime (JP); Tsuyoshi Takahashi, Ehime (JP)

(73) Assignee: Panasonic Healthcare Holdings Co., Ltd., Tokyo (JP)

( * ) Notice: Subject to any disclaimer, the term of this patent is extended or adjusted under 35 U.S.C. 154(b) by 0 days.

(21) Appl. No.: 14/003,090

(22) PCT Filed: May 10, 2012

(86) PCT No.: PCT/JP2012/003072
§ 371 (c)(1),
(2), (4) Date: Sep. 4, 2013

(87) PCT Pub. No.: WO2012/153535
PCT Pub. Date: Nov. 15, 2012

(65) Prior Publication Data
US 2013/0337571 A1    Dec. 19, 2013

(30) Foreign Application Priority Data
May 10, 2011    (JP) .................................. 2011-104990

(51) Int. Cl.
*G01N 33/66* (2006.01)
*G01N 27/327* (2006.01)
*G01N 33/00* (2006.01)

(52) U.S. Cl.
CPC ............ *G01N 33/66* (2013.01); *G01N 27/3273* (2013.01); *G01N 27/3274* (2013.01); *Y10T 436/144444* (2015.01)

(58) Field of Classification Search
CPC  G01N 27/3273; G01N 27/3274; G01N 33/66

USPC ........ 436/95; 422/82.01; 205/775; 204/403.1
See application file for complete search history.

(56) References Cited

U.S. PATENT DOCUMENTS 5,352,351 A    10/1994    White et al.
5,620,579 A    4/1997    Genshaw et al.
(Continued)

FOREIGN PATENT DOCUMENTS

CN    1558224    12/2004
CN    1589400    3/2005
(Continued)

OTHER PUBLICATIONS

International Search Report issued Jun. 12, 2012 in International (PCT) Application No. PCT/JP2012/003072.
(Continued)

*Primary Examiner* — Rebecca M Fritchman
(74) *Attorney, Agent, or Firm* — Wenderoth, Lind & Ponack, L.L.P.

(57) ABSTRACT

With this biological sample measuring device, the determination section performs measurement at specific intervals in a first measurement period from the start of measurement until a first time, and performs measurement at specific intervals in a second measurement period that comes after the first measurement period, calculates the difference between the measurement values in corresponding specific periods, and finds a plurality of first difference determination values, on the basis of a plurality of current values measured in the first measurement period and a plurality of current values measured in the second measurement period, finds a second difference determination value by finding the difference at specific intervals in the plurality of first difference determination values, and determines whether or not a reagent movement error and/or exposure error of the biological sample measurement sensor has occurred, on the basis of the first and second difference determination values.

10 Claims, 17 Drawing Sheets

(56) References Cited

U.S. PATENT DOCUMENTS

| | | | |
|---|---|---|---|
| 5,653,863 | A | 8/1997 | Genshaw et al. |
| 6,576,117 | B1 | 6/2003 | Iketaki et al. |
| 7,008,525 | B2 | 3/2006 | Morita et al. |
| 7,132,041 | B2 | 11/2006 | Deng et al. |
| 7,595,149 | B1 * | 9/2009 | Anderson et al. ............ 435/4 |
| 8,002,965 | B2 | 8/2011 | Beer et al. |
| 8,702,926 | B2 | 4/2014 | Beer et al. |
| 2004/0154932 | A1 | 8/2004 | Deng et al. |
| 2005/0067301 | A1 * | 3/2005 | Morita et al. ............ 205/775 |
| 2009/0014339 | A1 | 1/2009 | Beer et al. |
| 2009/0205967 | A1 * | 8/2009 | Fredenberg et al. ........ 205/118 |
| 2009/0205976 | A1 | 8/2009 | Yoshioka et al. |
| 2010/0000880 | A1 | 1/2010 | Itoh et al. |
| 2011/0262942 | A1 | 10/2011 | Beer et al. |
| 2014/0147872 | A1 | 5/2014 | Beer et al. |

FOREIGN PATENT DOCUMENTS

| | | |
|---|---|---|
| CN | 101180403 | 5/2008 |
| CN | 101495857 | 7/2009 |
| EP | 1 455 182 | 9/2004 |
| EP | 2 053 388 | 4/2009 |
| EP | 2 053 389 | 4/2009 |
| JP | 8-502589 | 3/1996 |
| JP | 8-304340 | 11/1996 |
| JP | 2008-536125 | 9/2008 |
| WO | 99/60391 | 11/1999 |
| WO | 03/044513 | 5/2003 |
| WO | 2008/013225 | 1/2008 |

OTHER PUBLICATIONS

Office Action issued Jul. 1, 2014 in corresponding Chinese application No. 201280010199.5, with English translation.

Supplementary European Search Report issued Aug. 7, 2014 in corresponding European Application No. 12782034.8.

\* cited by examiner

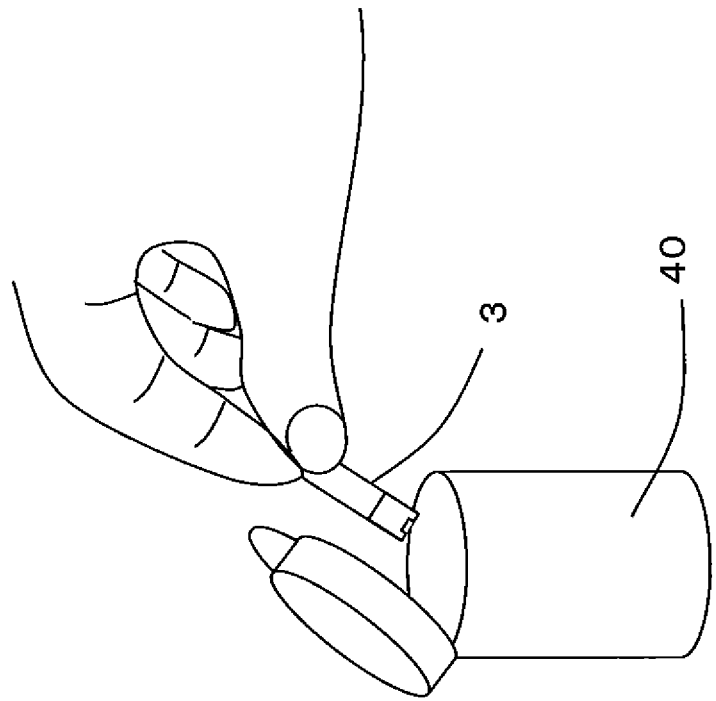
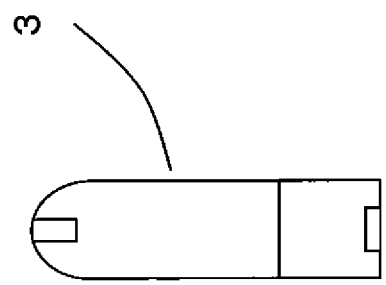
FIG. 3b
FIG. 3a

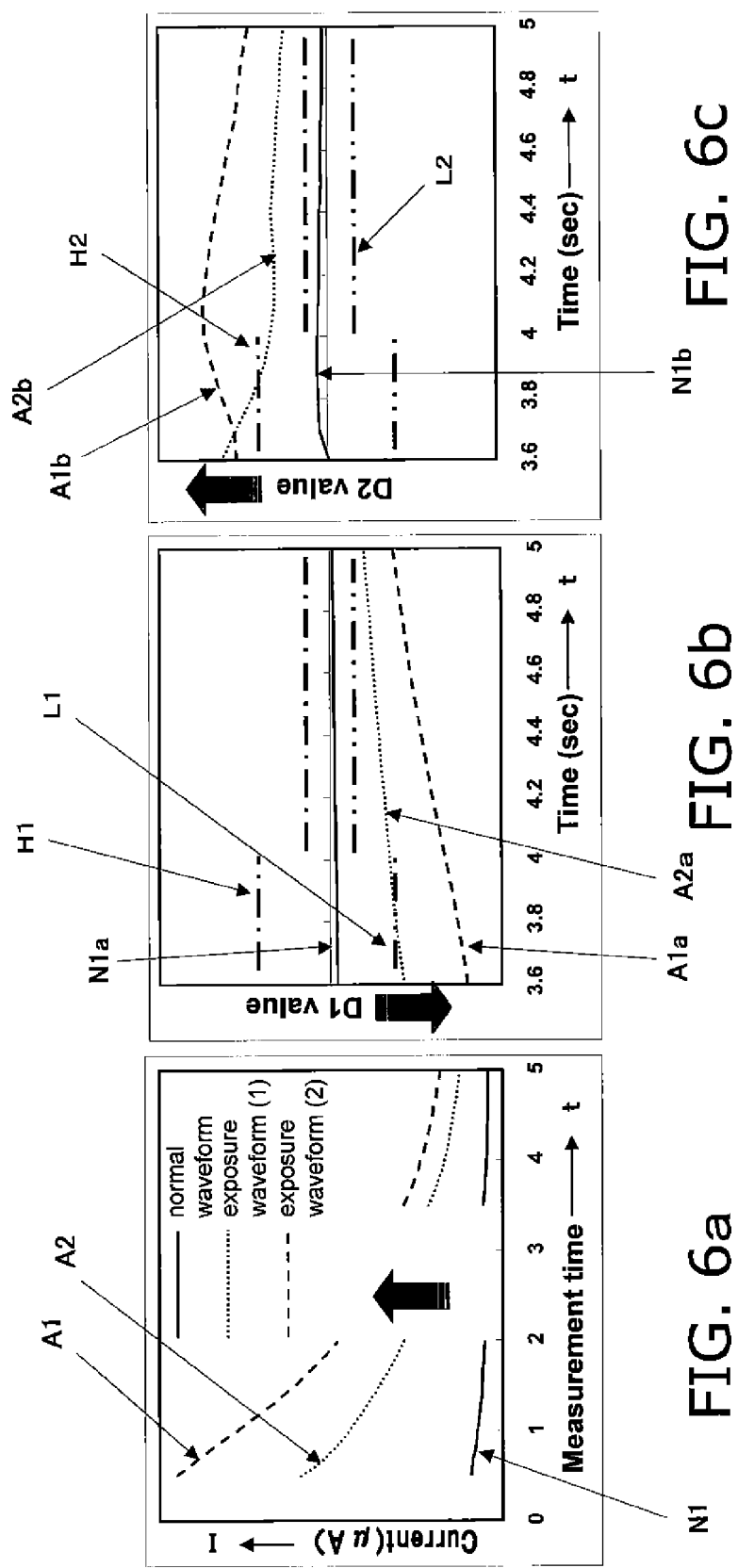

| D1(t) \ D2(t) | < L2, > H2 | < L2, ≤ H2 | ≥ L2, > H2 | ≥ L2, ≤ H2 |
|---|---|---|---|---|
| < L1, > H1 | E9 | E9 | E9 | E9 |
| < L1, ≤ H1 | E9 | E9 | E7 | E7 |
| ≥ L1, > H1 | E9 | E9 | E9 | E9 |
| ≥ L1, ≤ H1 | E9 | E9 | E9 | OK |

E7: exposure error
E9: reagent movement error

FIG. 11

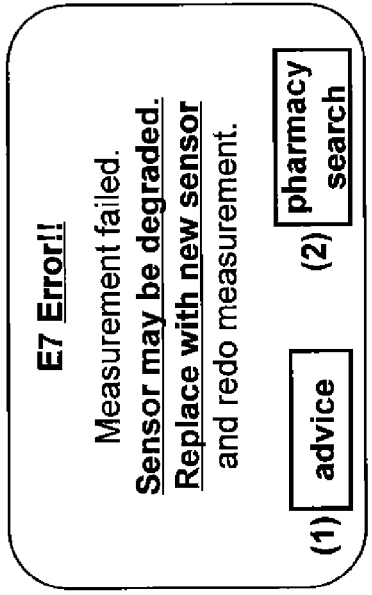
FIG. 12a
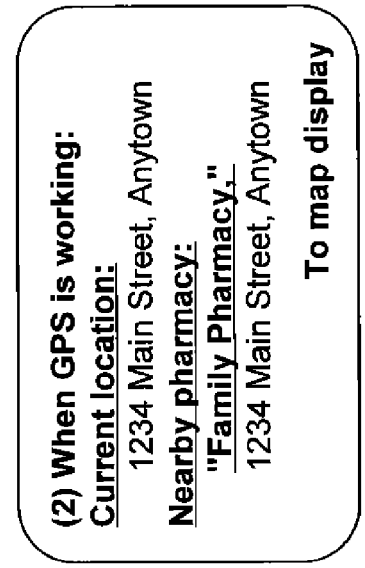
FIG. 12b
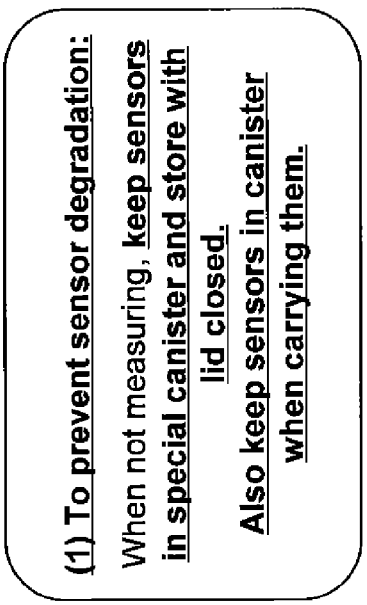
FIG. 12c
FIG. 12d

E9 Error!!

Measurement failed.
Error occurred during measurement.
Reinstall another sensor and redo measurement.

[advice]

FIG. 13b

Warning

Keep device and sensors safe from impact during measurement!!
Perform measurement in a stable state.

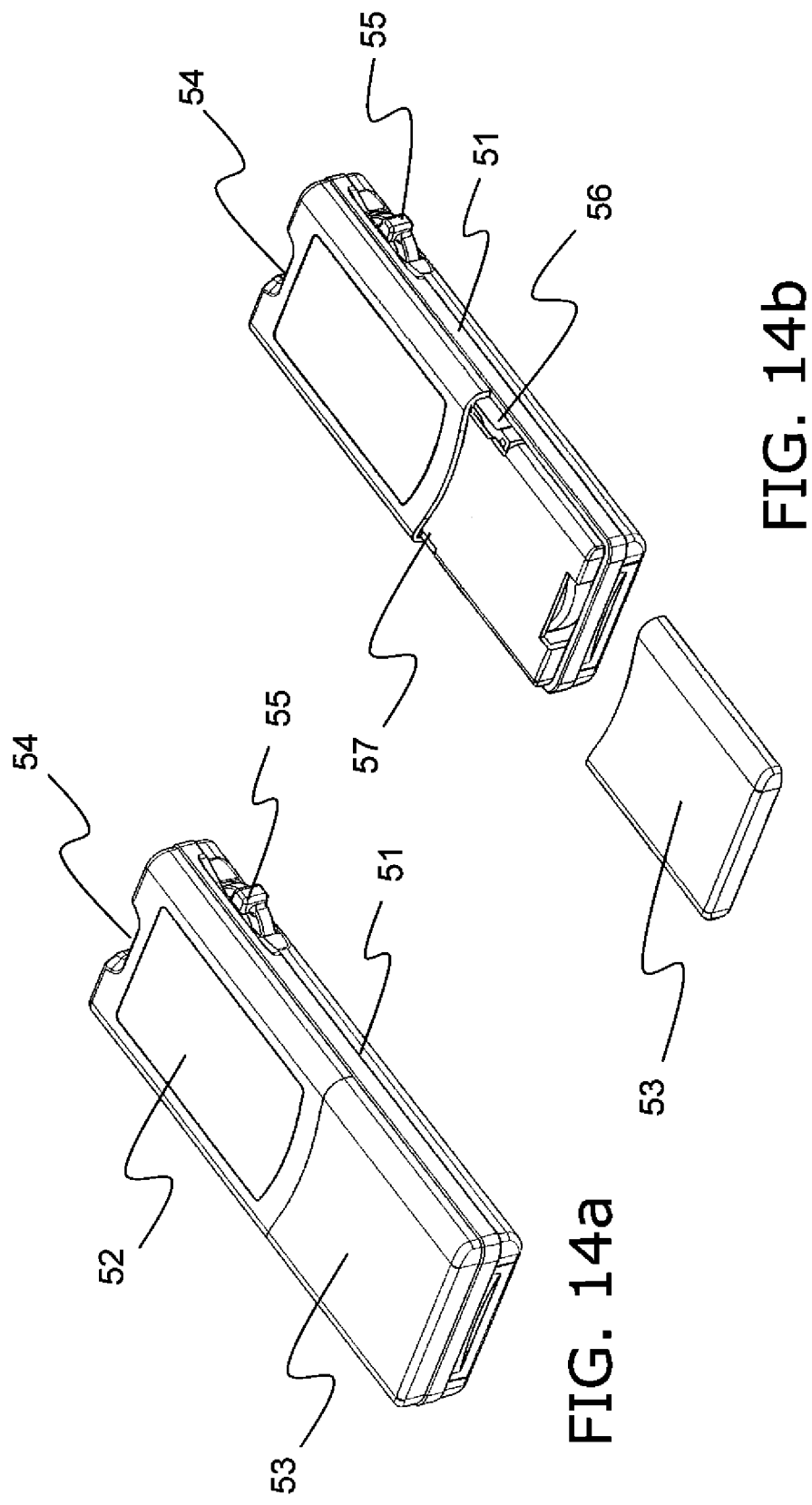

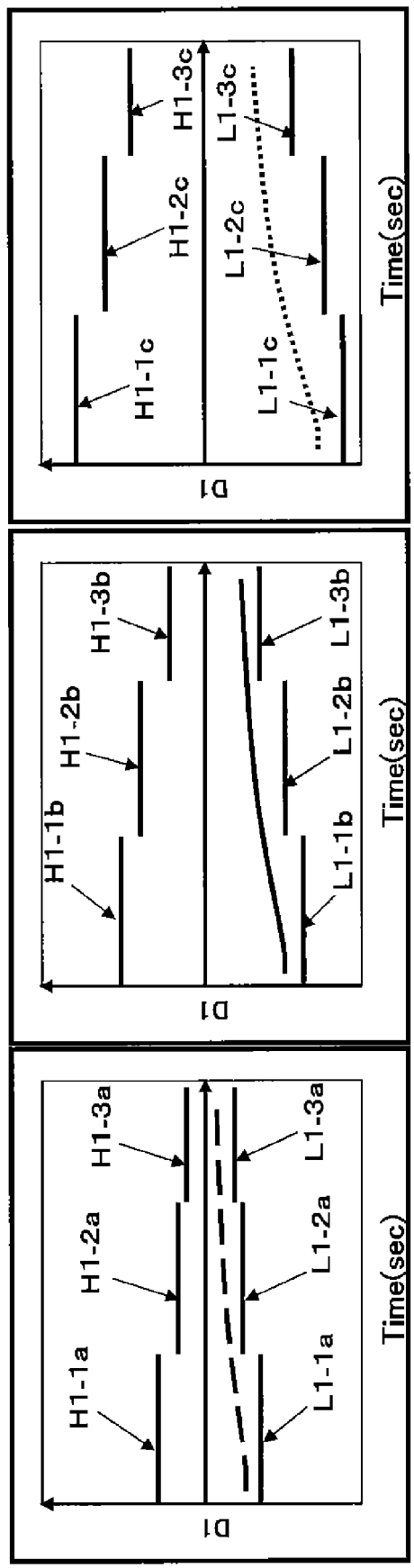

BIOLOGICAL SAMPLE MEASURING DEVICE AND METHOD FOR MEASURING BIOLOGICAL SAMPLE USING SAME

TECHNICAL FIELD

The present invention relates to a biological sample measuring device for measuring blood glucose levels, for example, and to a biological sample measurement method in which this device is used.

BACKGROUND ART

A conventional biological sample measuring device of this type was configured as follows.

A conventional biological sample measuring device comprised a main body case having a sensor mounting section to which a biological sample measurement sensor was mounted, a measurement section that was connected to the sensor mounting section of the main body case, a controller that was connected to the measurement section, and a determination section and display section that were connected to the controller. With a conventional biological sample measuring device, the voltage application pattern in which voltage is applied to an electrode system (working electrode, counter electrode, etc.) provided to a biological sample measurement sensor has a first application period and a second application period. The reduction current measurement value for the first application period and the reduction current measurement value for the second application period are compared, and if the difference between the two is outside a specific range, no measurement value is outputted (see Patent Literature 1 below, for example).

CITATION LIST

Patent Literature

Patent Literature 1: International Laid-Open Patent Application 2008/013225

SUMMARY

As discussed above, with the configuration of a conventional biological sample measuring device, the voltage application pattern in which voltage is applied to an electrode system (working electrode, counter electrode, etc.) provided to a biological sample measurement sensor has a first application period and a second application period. With the above-mentioned conventional biological sample measuring device, the reduction current measurement value for the first application period and the reduction current measurement value for the second application period are compared, and if the difference between the two is outside a specific range, the waveform is concluded to be abnormal, and no measurement value is outputted. With this configuration, however, details about the error, such as the type of error, could not be determined. This made it difficult to take the appropriate measures after the occurrence of an error, and ended up wasting time and biological sample measurement sensors.

Technical Problem

In view of this, it is an object of the present invention to provide a biological sample measuring device and a biological sample measurement method with which details about an error can be ascertained so that the user can take the appropriate measures to deal with the detected error.

Solution to Problem

To achieve this object, the biological sample measuring device of the present invention comprises a sensor mounting section to which a biological sample measurement sensor is mounted, a main body case having the sensor mounting section, a measurement section connected to the sensor mounting section, a controller connected to the measurement section, and a determination section and display section connected to the controller. The measurement section performs measurement at specific intervals in a first measurement period from the start of measurement until a first time, and performs measurement at specific intervals in a second measurement period that comes after the first measurement period. The determination section calculates the difference between the measurement values in corresponding specific periods, and finds a plurality of first difference determination values, on the basis of a plurality of current values measured in the first measurement period and a plurality of current values measured in the second measurement period. The determination section also finds a second difference determination value by finding the difference at specific intervals in a plurality of first difference determination values, and determines whether or not a reagent movement error and/or exposure error of the biological sample measurement sensor has occurred, on the basis of the first and second difference determination values.

The biological sample measurement method of the present invention makes use of a biological sample measuring device comprising a sensor mounting section to which a biological sample measurement sensor is mounted, a main body case having the sensor mounting section, a measurement section connected to the sensor mounting section, a controller connected to the measurement section, and a determination section and display section connected to the controller, said method comprising the following steps.

A step of performing measurement at specific intervals in a first measurement period from the start of measurement until a first time, and measurement at specific intervals in a second measurement period that comes after the first measurement period.

A step of calculating the difference between the measurement values in corresponding specific periods, and finding a plurality of first difference determination values, on the basis of a plurality of current values measured in the first measurement period and a plurality of current values measured in the second measurement period.

A step of finding a second difference determination value by finding the difference at specific intervals in a plurality of first difference determination values, and determining whether or not a reagent movement error and/or exposure error of the biological sample measurement sensor has occurred, on the basis of the first and second difference determination values.

Advantageous Effects

Because the precise type of error can be identified with the biological sample measuring device of the present invention, the user can take appropriate measures after an error has been detected, so less of the user's time is taken up after error detection, and waste of biological sample measurement sensors is eliminated.

BRIEF DESCRIPTION OF DRAWINGS

FIG. 3a is a plan view of a biological sample measurement sensor, and FIG. 3b is an oblique view of the state when the biological sample measurement sensor is removed from a sensor canister;

FIG. 6a is a graph of an abnormal waveform with the biological sample measuring device in an embodiment, FIG. 6b is a graph of the change in the abnormal determination value thereof, and FIG. 6c is a graph of the change in the abnormal measurement value thereof;

FIG. 11 is a table of error classification with the biological sample measuring device in this embodiment;

FIGS. 12a, 12b, 12c, and 12d are diagrams of display examples when an exposure error has occurred with the biological sample measuring device in this embodiment;

FIGS. 13a, 13b, and 13c are diagrams of display examples when a reagent movement error has occurred with the biological sample measuring device in this embodiment;

FIGS. 14a and 14b are oblique views of another biological sample measuring device pertaining to another embodiment of the present invention;

FIGS. 16a, 16b, and 16c are graphs of examples of setting a threshold in three stages for a waveform exhibiting changes in the first difference determination value under conditions in which the reaction proceeds slowly during normal measurement, under normal conditions, and under conditions in which the reaction proceeds readily;

DESCRIPTION OF EMBODIMENTS

The present invention will be described through reference to the appended drawings, for an embodiment in which the present invention is applied to a biological sample measuring device for measuring blood glucose levels.

In this embodiment, we will describe two types of abnormal waveform error, namely, exposure error and reagent movement error, as examples of abnormal waveform errors that can be detected with a biological sample measuring device.

The term "exposure error" here refers to an abnormal waveform error that is attributable to degradation of the performance of a biological sample measurement sensor 3 by moisture contained in outside air, which is the result of the biological sample measurement sensor 3 not being stored in the proper state in a sensor canister 40, the vessel being left open in the case of a individually packaged type, or another such reason. A characteristic of this is that since the moisture reacts with the reagent disposed in the measurement section of the biological sample measurement sensor 3, the obtained values tend to be uniformly greater than those of the correct waveforms.

The term "reagent movement error" refers to an abnormal waveform error that occurs when an impact or the like from the outside of the biological sample measurement sensor 3 causes a reagent 34 (see FIG. 4) to shift away from the position where it is supposed to be. A characteristic of this is that the change tends to be greater at certain points in time, as opposed to the uniform change encountered with an abnormal waveform when the above-mentioned exposure error occurs.

Embodiment 1

Figure 1:
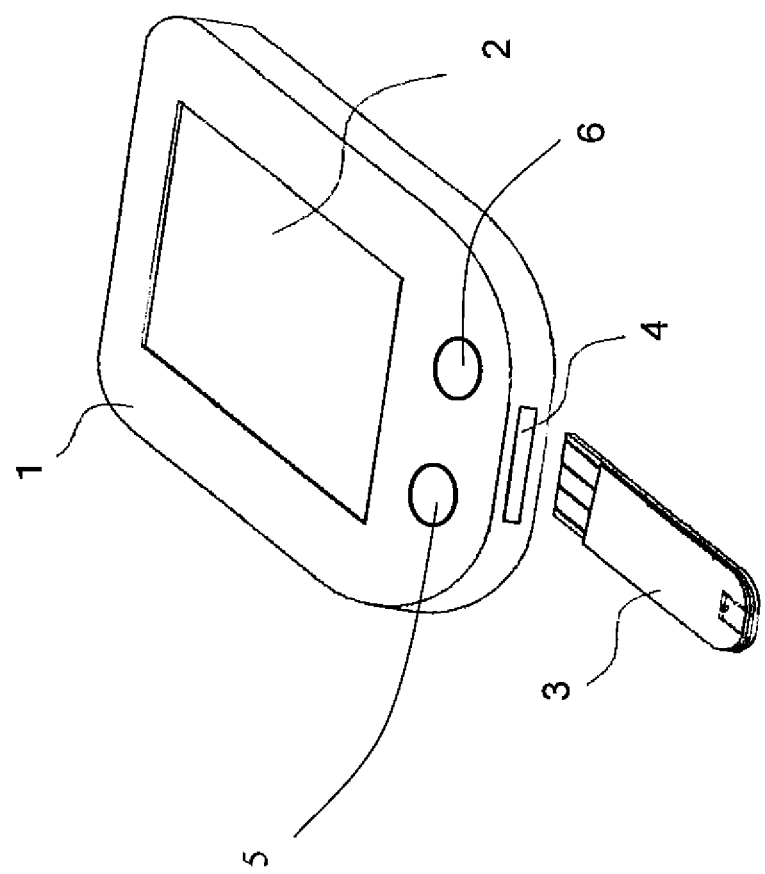
FIG. 1 is an oblique view of the configuration of the biological sample measuring device pertaining to an embodiment of the present invention.

FIG. 1 is an oblique view of the configuration of the biological sample measuring device pertaining to this embodiment.

As shown in FIG. 1, the biological sample measuring device comprises a main body case 1, a display section 2, a sensor insertion opening 4, and control buttons 5 and 6.

The main body case 1 has at one end the sensor insertion opening 4, into which the biological sample measurement sensor 3 is inserted. The control button 5, which is used to turn on the power to the display section 2, the control button 6, which is used to check the history of measurement data and so forth, and the like are provided to the front of the main body case 1.

Figure 2:
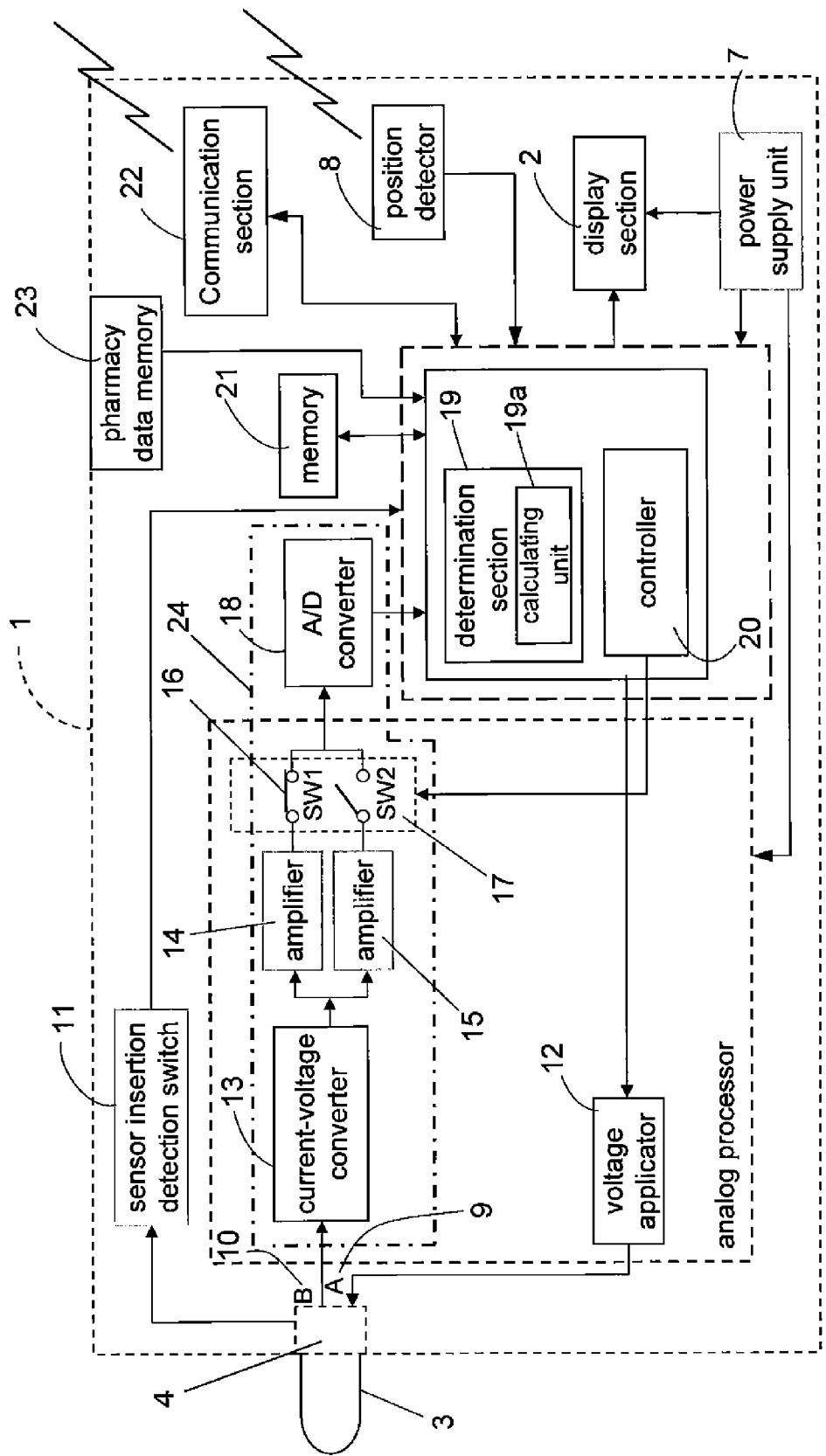
FIG. 2 is a block diagram of the electrical circuitry inside the biological sample measuring device in FIG. 1.

FIG. 2 is an electrical block diagram of this biological sample measuring device. The control buttons 5 and 6 provided to this biological sample measuring device are ordinary buttons, and therefore are not depicted in FIG. 2, in order to keep the drawing from being too complicated.

As shown in FIG. 2, connection terminals 9 and 10 are provided to the sensor insertion opening 4. The connection terminals 9 and 10 are connected to a voltage applicator 12 for applying voltage to the biological sample measurement sensor 3, and to a current-voltage converter 13, via the connection terminals 9 and 10.

As shown in FIG. 2, the voltage applicator 12 applies a specific voltage to the biological sample measurement sensor 3 on the basis of a command from a controller 20. At this point, the current inputted from the biological sample measurement sensor 3 through the connection terminals 9 and 10 is converted into voltage by the current-voltage converter 13, after which it is amplified by either an amplifier 14 or an amplifier 15, which are selectively switched by switches 16 and 17. The amplified signal is converted into a digital signal by an A/D (analog/digital) converter 18, and the converted digital signal is inputted to a determination section 19.

The digital signals inputted at specific time intervals to the determination section 19 are stored in a memory 21.

This operation is performed continuously during a first application period (T1; see FIG. 5*a*) and a second application period (T2; see FIG. 5*a*), and the input data (the above-mentioned digital signal) is held in the memory 21.

A calculating unit 19*a* uses the following formula (1) to calculate first and second abnormal determination values D1-1 and D1-2 (a plurality of first difference determination values) on the basis of the input data held in the memory 21. It also uses the following formula (2) to calculate a third abnormal determination value (D2) (second difference determination value).

$$D1(t)=X(t)-X(t-\alpha) \quad (1)$$

(t: variable expressing time, α: constant)

$$D2(t)=D1(t)-D(t-\beta) \quad (2)$$

(t: variable expressing time, β: constant)

Here, X(t) is the above-mentioned digital signal in the above-mentioned second application period (T2; see FIG. 5*a*), and X(t−α) is the above-mentioned digital signal in the above-mentioned first application time (T1; see FIG. 5*a*), which is prior to the second application period by a specific length of time α (constant). In FIG. 5*b*, α=3 sec.

Here, the phrase "digital signal in the first application period" means the measurement value for the portion t=0 to 2 sec in FIG. 5*b*. The phrase "digital signal in the second application period" means the measurement value for the portion t=3 to 5 sec (t is a variable expressing time) in FIG. 5*b*.

P1 in FIG. 5*b* is the point at which the blood glucose level is measured. In this embodiment, instead of making a decision by continuously taking in data for a specific length of time as with the above-mentioned method for detecting an abnormal waveform error, measurement data at the end point of the second application time T2 shown in FIG. 5*a* (in this example, the point P1 at t=5 sec) is used in blood glucose level measurement.

The first abnormal determination value D1-1 indicates an abnormal determination value D1(t1) which is the difference between the measurement value (digital value) X(t1) at the time t1 and the measurement value (digital value) X(t1−α) at the time t1−α. The second abnormal determination value D1-2 indicates an abnormal determination value D1(t2) which is the difference between the measurement value (digital value) X(t2) at the time t2 and the measurement value (digital value) X(t2−α) at the time t2−α. If we plug specific values into Formula 1 above (in this example, α=3 sec), the first abnormal determination value D1(t1) at the time t1 is expressed by:

$$D1\text{-}1=D1(t1)=X(t1)-X(t1-3)$$

and the second abnormal determination value D1(t2) at the time t2 by:

$$D1\text{-}2=D1(t2)=X(t2)-X(t2-3)$$

Formula 1 above is found by using the first abnormal determination value D1(t1) and the second abnormal determination value D1(t2) found by computing from Formula 1 above.

Here, a constant time interval β indicates the time difference between t1 and t2. In this embodiment an example is given in which β=0.1 sec.

If we plug this into Formula 2 above, the third abnormal determination value D2 indicates the abnormal determination value D2(t3) at the time t3, and is expressed by:

$$D2=D2(t3)=D1(t3)-D1(t3-0.1)$$

With the biological sample measuring device in this embodiment, as discussed above, an abnormal waveform error is identified by using the first abnormal determination value D1(t1), the second abnormal determination value D1(t2), and the third abnormal determination value D2(t3) found from Formulas 1 and 2.

The determination section 19 performs identification of an abnormal waveform error on the basis of the first, second, and third abnormal determination values (D1(t1), D1(t2), and D2(t3)) calculated by the calculating unit 19*a*, and determination-use first lower threshold L1, first upper threshold H1, second lower threshold L2, and second upper threshold H2 for identifying abnormal waveform errors, which are preset and stored in the memory 21.

In this embodiment, an example is given in which these determination-use first lower threshold L1, first upper threshold H1, second lower threshold L2, and second upper threshold H2 are preset and stored in the memory 21, but these thresholds may, for example, be varied or switched on the basis of specific conditions. The varying and switching of these thresholds will be discussed below.

The first lower threshold L1, first upper threshold H1, second lower threshold L2, and second upper threshold H2 here are set by measuring normal values under various conditions for factors that are expected to cause variation in specific blood glucose level, hematocrit value, or the like, and statistically estimating variation in normal values caused by conditions on the basis of the averages and standard deviations in these normal values.

The controller 20 displays the abnormal waveform error identification result identified by the determination section 19, on the display section 2 provided to the front of the main body case 1.

The display section 2 is able to produce a segment display or a dot matrix display, and gives a segment display of exposure error and reagent movement error detection results as errors that can be detected and identified with this biological sample measuring device (see FIGS. 11 and 12). More specifically, the display section 2 displays corresponding error codes or other such segments. If the display section 2 produces a dot matrix display, it displays a corresponding error message as well as instructions for how to deal with the error, etc., and notifies the user. An option here is to provide a sound output section (a buzzer, small speaker, etc.) so that the user can be notified of error detection results and so forth audibly (by sound).

In the case of an exposure error, depending on the nature thereof, there is the risk that all of the biological sample measurement sensors 3 carried by the user will become defective. Accordingly, if exposure errors are continuously detected a number of times in a row, there is also a function for displaying assistance in purchasing new sensors from a nearby pharmacy (see FIG. 12*d*).

More specifically, in FIG. 2, a position detector 8 has a GPS function, so the current location can be ascertained and this information displayed on the display section 2. A communication section 22 wirelessly accesses an external pharmacy database, which can be used to find out if there is a pharmacy located nearby, whether the relevant biological sample measurement sensor 3 is in stock, and so forth. Also, instead of using the communication section 22, a pharmacy data memory (memory slot) may be provided to the main body case 1. In this case, pharmacy data stored in an SD memory or the like is inputted so that a pharmacy search can be performed.

FIG. 3 illustrates how this biological sample measuring device is used.

Usually, the user carries around a sensor canister 40 holding biological sample measurement sensors 3, takes a biological sample measurement sensor 3 out of the sensor canister 40, and uses it to measure blood glucose level, etc. In general, a biological sample measurement sensor's performance tends to be degraded by moisture. Thus, a desiccant or other such preservative (not shown) is kept inside the sensor canister 40 to prevent degradation of the biological sample measurement sensors.

In the above description, an example was given in which the biological sample measurement sensors 3 were kept in the sensor canister 40, but the present invention is not limited to this. For example, instead of keeping the sensors in a sensor canister, they may be an individually packaged type, in which the biological sample measurement sensors 3 are individually packaged. In this case, the biological sample measurement sensors are carried around in their individually packaged state, and when it is time for measurement, the user opens up one of the packages, takes out the biological sample measurement sensor 3 held inside, and can then measure blood glucose level or the like.

Similarly, a biological sample measurement sensor and a desiccant may be sealed inside an individual packaging material in order to prevent performance degradation by moisture.

In this embodiment, it can be concluded that an exposure error has occurred if, for example, the biological sample measurement sensor 3 has not been stored properly inside the sensor canister 40 (such as when the sensor canister 40 is carried around without its lid 41 at the top being properly closed, or when the biological sample measurement sensor 3 has been taken out of the sensor canister 40 and left out, or when an individually packaged type has been opened and left out).

Figure 4:
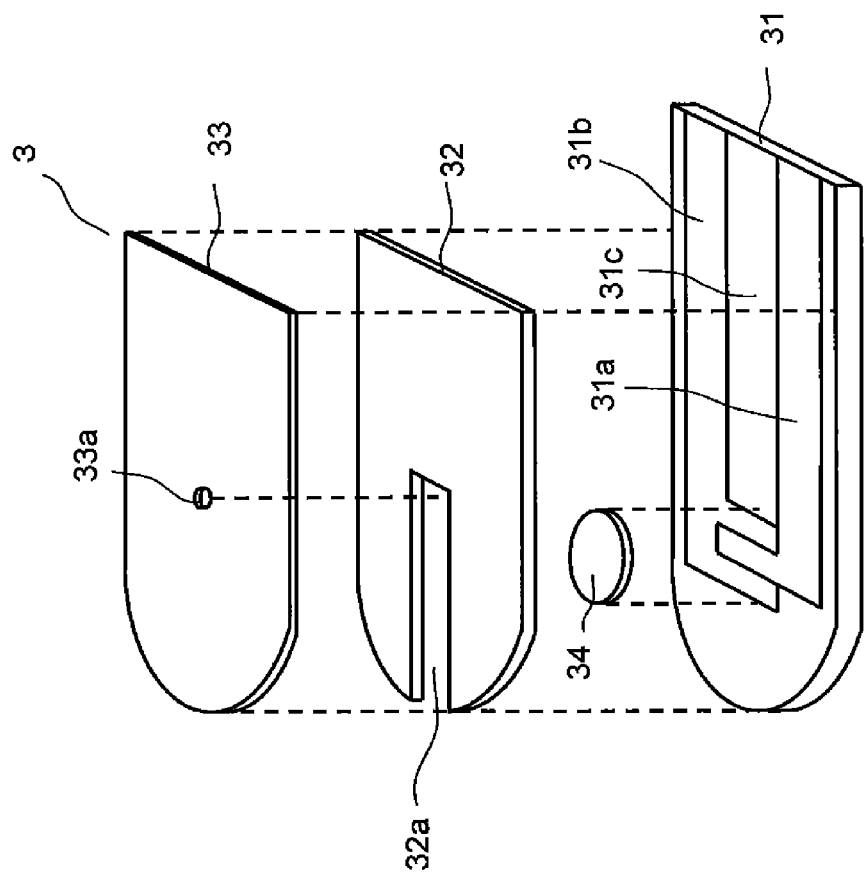
FIG. 4 is an exploded oblique view of the configuration of the biological sample measurement sensor in FIG. 3.

FIG. 4 is an exploded oblique view of the configuration of the biological sample measurement sensor 3.

The biological sample measurement sensor 3 has electrodes 31a, 31b, and 31c disposed opposite each other and at a specific spacing on a rectangular board 31. The electrodes 31a, 31b, and 31c are provided at one end of the board 31 (on the right side in FIG. 4), so that the electrodes 31a, 31b, and 31c come into contact with the connection terminals 9 and 10 provided inside the sensor insertion opening 4 shown in FIG. 1. This allows the biological sample measurement sensor 3 to be electrically connected with the electrical circuit inside the main body case 1.

The reagent 34 is disposed at the other end of the board 31 (the left side in FIG. 4) so as to straddle the electrodes 31a, 31b, and 31c.

There are three electrodes here (the electrodes 31a, 31b, and 31c), but measurement will be possible as long as there are two electrodes (a working electrode 31a and a counter electrode 31b). The other electrode is used as a detecting electrode 31c that detects the introduction of blood.

Similarly, the connection terminals 9 and 10 on the main body case 1 side are only mentioned at two places here, but actually other connection terminals (not shown) are provided for the detecting electrode 31c, etc.

Furthermore, a cover 33 is disposed via a spacer 32 so as to cover the reagent 34 portion of the board 31.

As shown in FIG. 4, the spacer 32 has a slit 32a formed in it so as to go across the reagent 34. Consequently, the electrodes 31a, 31b, and 31c and the reagent 34 are in a state in which they face the space inside the slit 32a.

Consequently, by disposing the cover 33 on the upper side of the spacer 32 having the slit 32a, and the board 31 on the lower side, the slit 32a portion forms a space that serves as a capillary (supply path) for the blood or the like that is to be measured. The reagent 34 and the electrodes 31a, 31b, and 31c are disposed at locations facing the capillary so that the introduction of blood will be detected by the detecting electrode 31c, and electrical signals produced by a reaction between the blood and the reagent 34 will be detected and measured by the electrodes 31a and 31b, allowing the blood glucose level, etc., to be measured.

The cover 33 is disposed over the spacer 32. A space hole 33a is formed in the portion of the cover 33 corresponding to the slit 32a.

The space hole 33a communicates with the above-mentioned capillary, and its purpose is to assist in introducing the blood to the capillary by capillary action.

As shown in FIG. 3b, in the above configuration, prior to use the biological sample measurement sensors 3 are stored in the sensor canister 40 (see FIG. 3), which is a dry container. The biological sample measurement sensors 3 are taken out of the sensor canister 40 one by one whenever the blood glucose level is measured. Then, as shown in FIG. 1, one end of the biological sample measurement sensor 3 is inserted into the sensor insertion opening 4 and electrically connected to the electrical circuit in the main body case 1 via the connection terminals 9 and 10 (in this state, the user's blood is not yet supplied to the slit 32a portion).

Once this state is achieved, the controller 20 applies a specific voltage between the electrodes 31a and 31b of the biological sample measurement sensor 3 via the voltage applicator 12 and the connection terminals 9 and 10.

Method for Identifying Exposure Error

Next, the method for identifying an exposure error will be described through reference to FIGS. 6a, 6b, and 6c. FIG. 6a is a typical example of the waveform when an exposure error occurs. N1 in FIG. 6a shows the change in the measurement value under normal circumstances (normal waveform), and A1 and A2 both show the change in the measurement value when an exposure error has occurred (exposure waveforms 1 and 2).

Here, the waveform when an exposure error occurs tends to exhibit a larger value than normal (the value for a large reaction current shown on the Y axis in FIG. 6a).

The waveforms shown in FIG. 6a correspond to the above-mentioned measurement values $X(t)$ and $X(t-\alpha)$. In this embodiment, the measurement range and so forth are as follows.

Figure 5A:
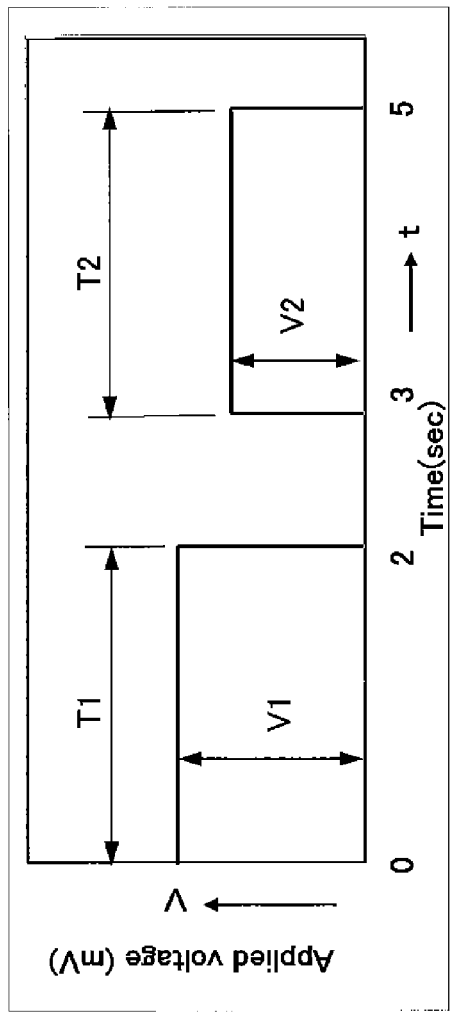
FIG. 5a is a graph of the voltage application pattern during normal measurement with the biological sample measuring device in FIG. 1.
Figure 5B:
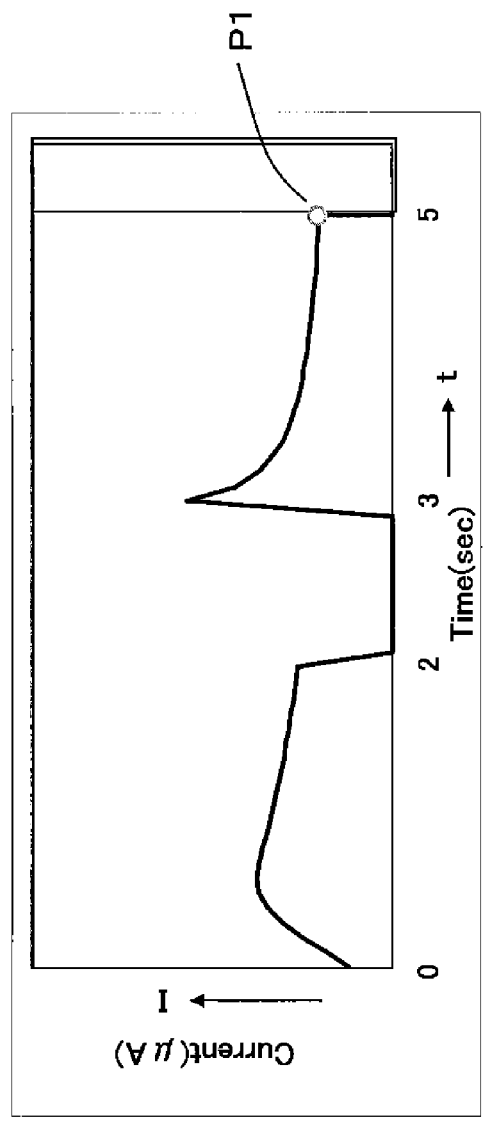
FIG. 5b is a graph of the waveform of the measurement input signal at this point.

The first measurement period indicates the measurement range in the first application time (T1) (see FIG. 5a). In this embodiment the range is time $t=0.6$ to 2 sec.

A first measurement value m1 and a second measurement value m2 serve as the measurement value $X(t-\alpha)$ in the first application period.

Similarly, the second measurement period indicates the measurement range in the second application period (T2) (see FIG. 5a). In this embodiment the second measurement period is a range in which the time $t=3.6$ to 5 sec. A third measurement value m3 and a fourth measurement value m4 serve as the measurement value $X(t)$ in the second measurement period. In this embodiment, the above-mentioned constant $\alpha$ is 3 sec.

Then, the first and second abnormal determination values $D1(t1)$ and $D1(t2)$ are computed using the above Formula 1, on the basis of the measurement values shown in FIG. 6a.

That is, the first abnormal determination value D1(t1) is found by calculating the difference in the first measurement value m1 in the first measurement period (a range of t=0.6 to 2 sec) from the third measurement value m3 in the second measurement period (a range of t=3.6 to 5 sec). Similarly, the second abnormal determination value D1(t2) is found by calculating the difference in the second measurement value m2 in the first measurement period from the fourth measurement value m4 in the second measurement period.

Specifically, the first abnormal determination value D1(t1) and the second abnormal determination value D1(t2) are found as in the following formulas.

$$D1(t1)=m3-m1$$

$$D1(t2)=m4-m2$$

The first to fourth measurement values m1 to m4 here are found as in the following respective formulas, since the constant α=3 sec.

$$m1=X(t1-3)$$

$$m2=X(t2-3)$$

$$m3=X(t1)$$

$$m4=X(t2)$$

Furthermore, since the first and third measurement values m1 and m3 are the first measurement value in their respective measurement periods, they are measurement values at a point when t1 is 3.6 sec after the start of measurement. Since the second and fourth measurement values m2 and m4 are the second measurement values in their respective measurement periods, they are measurement values at a point when t2 is 3.7 sec (in this example, the measurement interval is 0.1 sec). Thus, substitution yields the following.

$$D1(t1)=D1(3.6)=X(3.6)-X(0.6)$$

$$D1(t2)=D1(3.7)=X(3.7)-X(0.7)$$

The graph in FIG. 6b shows the change in the computed values for the first and second abnormal determination values D1(t1) found by repeating the above computation every 0.1 sec until t1 is between 3.6 and 5 sec.

As shown in FIG. 6b, the waveforms A1a and A2a (exposure waveforms 1 and 2), which indicate the change in the abnormal determination value D1(t) when an exposure error has occurred, are much more to the negative side than with the waveform N1a, which indicates the change in the normal waveform D1(t1).

H1 and L1 here are thresholds used for error identification, with H1 indicating the upper threshold of the first and second abnormal determination values D1, and L1 indicating the lower threshold of the first and second abnormal determination values D1.

The upper and lower thresholds of D1 are not constant over the entire period, and have a number of ranges, taking into account the change over time in the reaction related to measurement.

The third abnormal determination value D2(t3) will now be described.

The third abnormal determination value D2(t3) is found by using the first abnormal determination value D1(t1) computed from the above-mentioned Formula 1, and the second abnormal determination value D1(t2) computed from Formula 2.

Specifically, the third abnormal determination value D2(t3) is found as follows.

$$D2(t3)=D1(t3)-D1(t3\beta)$$

Next, if we apply the constant β (measurement interval)=0.1 sec and t3=3.6 to 5 sec, the data for the first D2(t3) is as follows.

$$D2(t3)=D2(3.6)=D1(3.6)-D1(3.5)$$

The computed value for D1 at the 3.5 sec point is not shown in FIG. 6b, but the data is computed as t0=3.5 and stored in the memory.

That is, the computed value for D1 at the 3.5 sec point is found from the following calculation formula.

$$D1(t0)=D1(3.5)=X(3.5)-X(0.5)$$

FIG. 6c is a graph of the change in the computed value for the third abnormal determination value D2(t3) found by repeating the above computation every 0.1 sec until t3 is between 3.6 and 5 sec.

As shown in FIG. 6c, the waveforms A1b and A2b (exposure waveforms 1 and 2), which indicate the change in D2(t3) when an exposure error has occurred, are much more to the positive side than with the waveform N1b, which indicates the change in the normal waveform D2(t3).

H2 and L2 here are thresholds used for error identification, with H2 indicating the upper threshold of the third abnormal determination value D2, and L2 indicating the lower threshold of the third abnormal determination value D2.

The upper and lower thresholds of D2 are not constant over the entire period, and have a number of ranges, taking into account the change over time in the reaction related to measurement.

With the biological sample measuring device in this embodiment, as discussed above, for the first and second abnormal determination values D1(t1) and D1(t2), a situation corresponding to the following conditions is determined to be an exposure error, on the basis of FIG. 6c, for the third abnormal determination value D2(t3).

More specifically, an exposure error is determined to have occurred in the biological sample measurement sensor 3 if the first or second abnormal determination value D1(t1) or D1(t2) is less than the first lower threshold L1, and the first and second abnormal determination values D1(t1) and D1(t2) are at or below the first upper threshold H1, and the third abnormal determination value D2(t3) is at or above the second lower threshold L2.

The absolute value of the second lower threshold L2 is less than the absolute values of the first lower threshold L1 and the first upper threshold H1.

Method for Identifying Reagent Movement Error

Next, the method for identifying a reagent movement error will be described through reference to FIGS. 7a, 7b, and 7c.

Figures 7A, 7B, 7C:
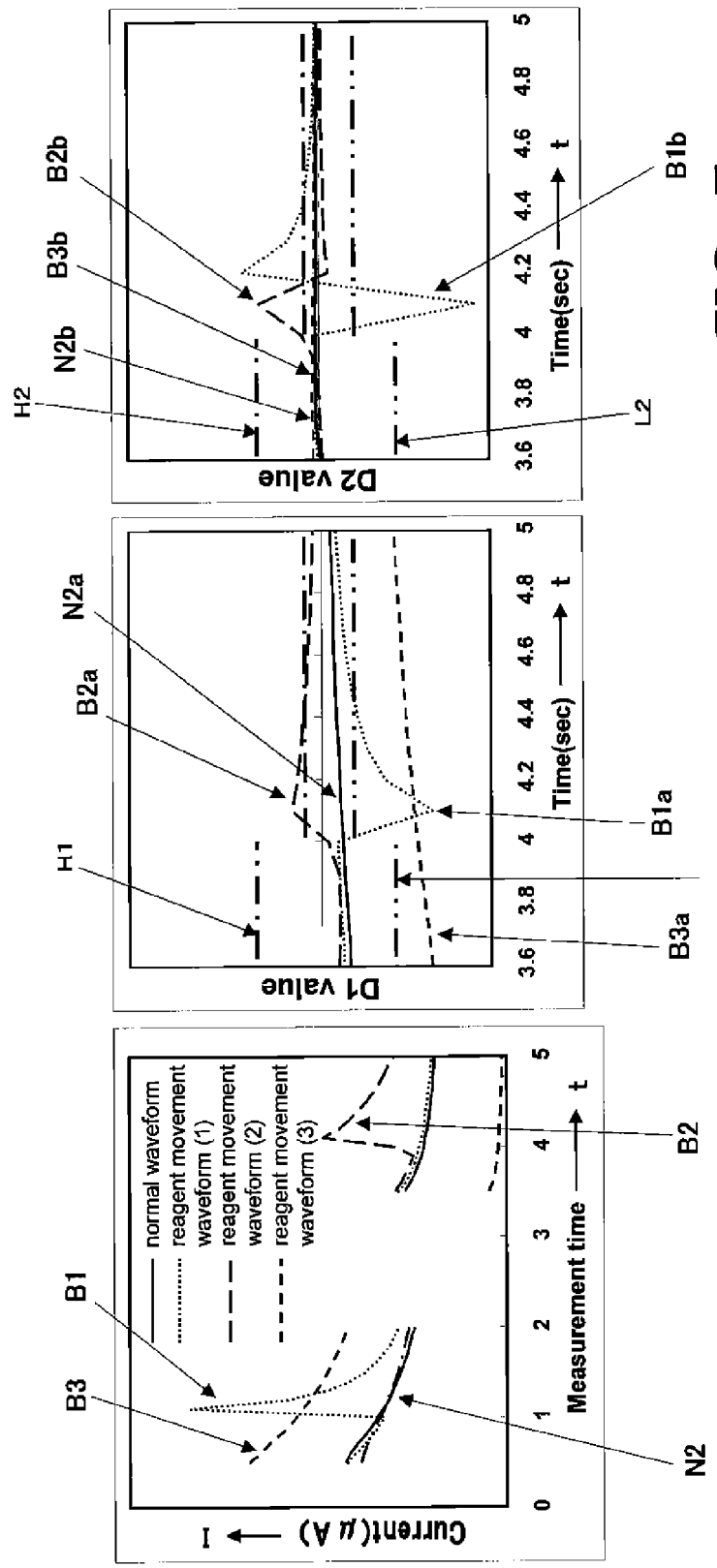
FIG. 7a is a graph of another abnormal waveform with the biological sample measuring device in this embodiment.
FIG. 7b is a graph of the change in the abnormal determination value thereof.
FIG. 7c is a graph of the change in the abnormal measurement value thereof.

First, FIG. 7a shows a normal waveform and typical examples of an abnormal waveform detected when the reagent 34 moves from its designated position in the biological sample measurement sensor 3.

N2 in FIG. 7a is a curve (solid line) indicating the change in the measurement value under normal circumstances. B1 to B3 are curves (dotted lines) indicating the change in the measurement value when reagent movement has occurred.

B1 shows the abnormal waveform detected when reagent movement has been caused by impact from the outside or the like, during the first application time T1 (see FIG. 5a). B2 shows the abnormal waveform detected when reagent movement has occurred during the second application time T2 (see FIG. 5a). B3 shows the abnormal waveform detected when reagent movement has occurred immediately prior to the first application time T1.

These waveforms detected when reagent movement has occurred are characterized by the fact that the detected value is higher at certain points in time, as opposed to the uniform change that occurs with an exposure error as discussed above.

The identification of a reagent movement error is carried out by using the methods for computing the first to third abnormal determination values D1(t1), D1(t2), and D2(t3), just as when an exposure error occurs, so this will not be described again here.

FIG. 7b is a graph of D1(t1) and D1(t2), and FIG. 7c a graph of D2(t3), which indicate the change in the above-mentioned abnormal determination values when reagent movement has occurred, and which are found using the computation formulas given above.

As shown in FIG. 7b, N2a is a normal curve, while B1a, B2a, and B3a are curves for when a reagent movement error has occurred, corresponding to B1, B2, and B3, respectively.

H1 is the upper threshold for D1, L1 is the lower threshold for D1, and what was described above for the method for identifying an exposure error is the same here.

FIG. 7c is a graph showing the change in the third abnormal determination value D2(t3). N2b is a normal curve, and B1b, B2b, and B3b are curves corresponding to B1a, B2a, and B3a, respectively.

Similarly, H2 is the upper threshold for D2, and L2 is the lower threshold for D2.

As discussed above, for the first and second abnormal determination values D1(t1) and D1(t2), a situation corresponding to the following conditions is determined to be a reagent movement error, on the basis of FIG. 7c, for the third abnormal determination value D2(t3).

More specifically, a reagent movement error is determined to have occurred in the biological sample measurement sensor 3 if the first abnormal determination value D1(t1) and second abnormal determination value D1(t2) found by computation using the above-mentioned Formula 1, and the third abnormal determination value D2(t3) found by computation using the above-mentioned Formula 2 are outside the following conditions (1) and (2).

(1) When the first or second abnormal determination value D1(t1) or D1(t2) is less than the first lower threshold L1, and the first and second abnormal determination values D1(t1) and D1(t2) are at or below the first upper threshold H1, and the third abnormal determination value D2(t3) is at or above the second lower threshold L2.

(2) When the first and second abnormal determination values D1(t1) and D1(t2) are at or above the first lower threshold L1 and at or below the first upper threshold H1, and the third abnormal determination value D2(t3) is at or above the second lower threshold L2 and at or below the second upper threshold H2.

Here, the absolute values of the second upper threshold H2 and the second lower threshold L2 are less than the absolute values of the first upper threshold H1 and the first lower threshold L1.

With the biological sample measuring device in this embodiment, whether or not a reagent movement error has occurred in the biological sample measurement sensor 3 is determined as above.

Next, the operation of the biological sample measuring device in this embodiment will be described through reference to FIGS. 8 to 10.

Figure 8:
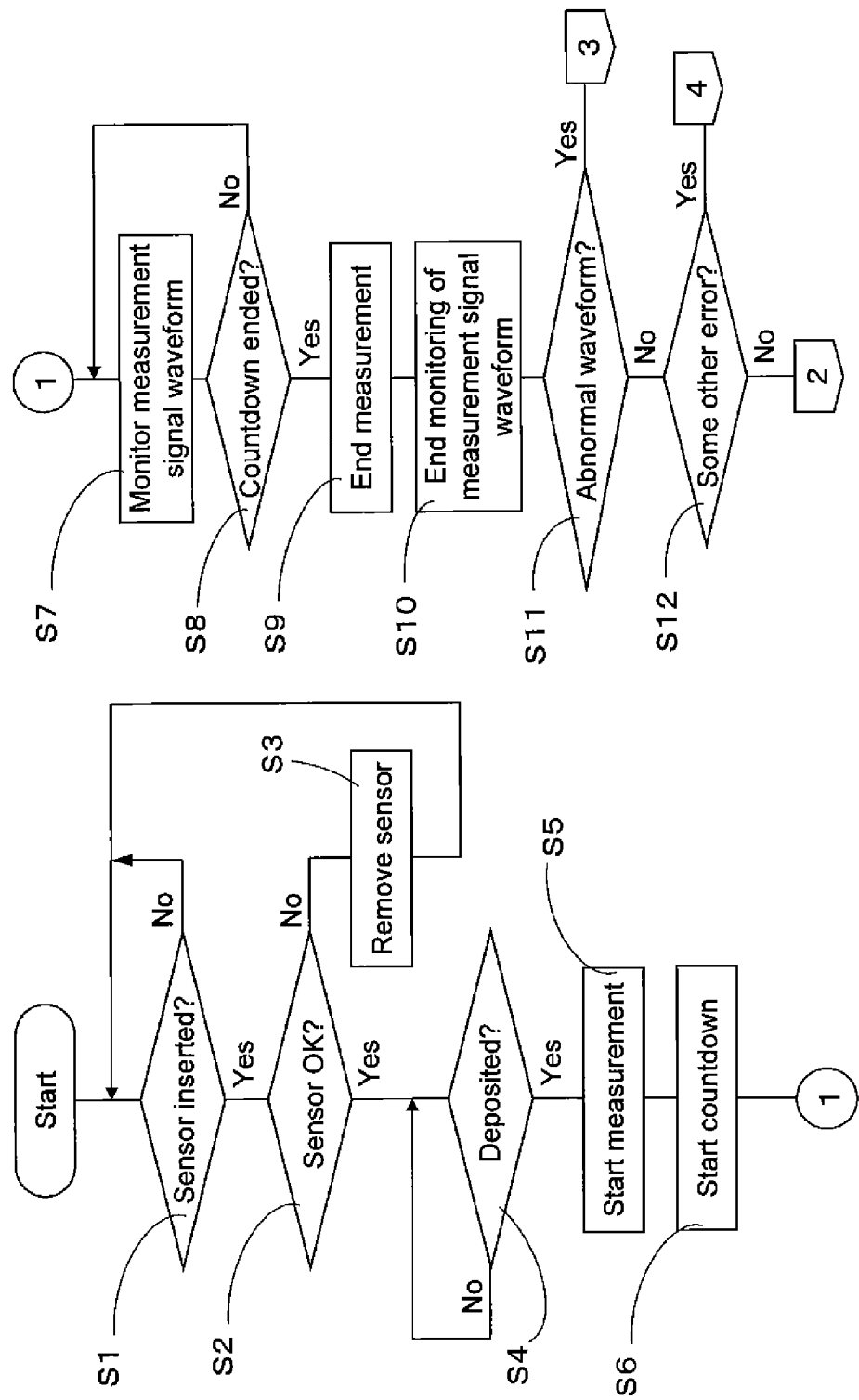
FIG. 8 is an operating flowchart of the biological sample measuring device in this embodiment.

First, the biological sample measurement sensor 3 is inserted into the sensor insertion opening 4 of the main body case 1 (S1 in FIG. 8).

Then, when it is detected that the biological sample measurement sensor has been inserted into the sensor insertion opening 4 (S1 in FIG. 8), the main power supply to the main body case 1 is switched on, and it is determined whether or not the proper biological sample measurement sensor 3 has been inserted (S2 in FIG. 8). This determination identifies whether the biological sample measurement sensor 3 has been inserted in the proper direction, whether the sensor has already been used, whether it is a different type of sensor, and so forth.

If the inserted biological sample measurement sensor 3 is found to be incorrect here, a display to that effect is given, and the biological sample measurement sensor 3 is taken out of the biological sample measurement sensor 3 (S3 in FIG. 8).

Next, if the biological sample measurement sensor 3 is found to be correct, the subjects skin is punctured with a separate puncture device, so that blood oozes out. This blood is deposited at one end of the biological sample measurement sensor 3 and introduced from there into the capillary, where it is measured for blood glucose level, etc. (S4 in FIG. 8).

It the deposit of blood has been confirmed, the measurement of blood glucose level is commenced (S5 in FIG. 8). Whether or not the blood deposited on the biological sample measurement sensor 3 has been properly introduced into the capillary can be ascertained by applying voltage to the detecting electrode 31c in FIG. 4 and detecting the output thereof.

Once the measurement of blood glucose level begins, it is continued for a specific length of time. The waiting time is displayed on the screen, and a countdown is begun (S6 in FIG. 8). During this countdown, measurement is performed at specific intervals to monitor the measurement signal waveform. The measurement values are stored in the memory 21 (see FIG. 2) (S7 in FIG. 8). This processing is continued until the end of the countdown (S8 in FIG. 8).

Once the countdown is over, the measurement is ended (S9 in FIG. 8). This also ends the monitoring of the waveform of the measurement signal. That is, the measurement at specific intervals is ended (S10 in FIG. 8).

After the measurement is over, it is determined whether there is an abnormal waveform error (S11 in FIG. 8) or some other error (S12 in FIG. 8), on the basis of the measurement values stored in the memory 21, the first to third abnormal determination values found using the above-mentioned Formulas 1 and 2, and the first upper threshold H1, the first lower threshold L1, the second upper threshold H2, and the second lower threshold L2. If there is some other error, the error details are displayed (S27 in FIG. 9), the biological sample measurement sensor 3 is taken out through the sensor insertion opening 4, and the measurement is ended (S17 in FIG. 9).

Figure 9:
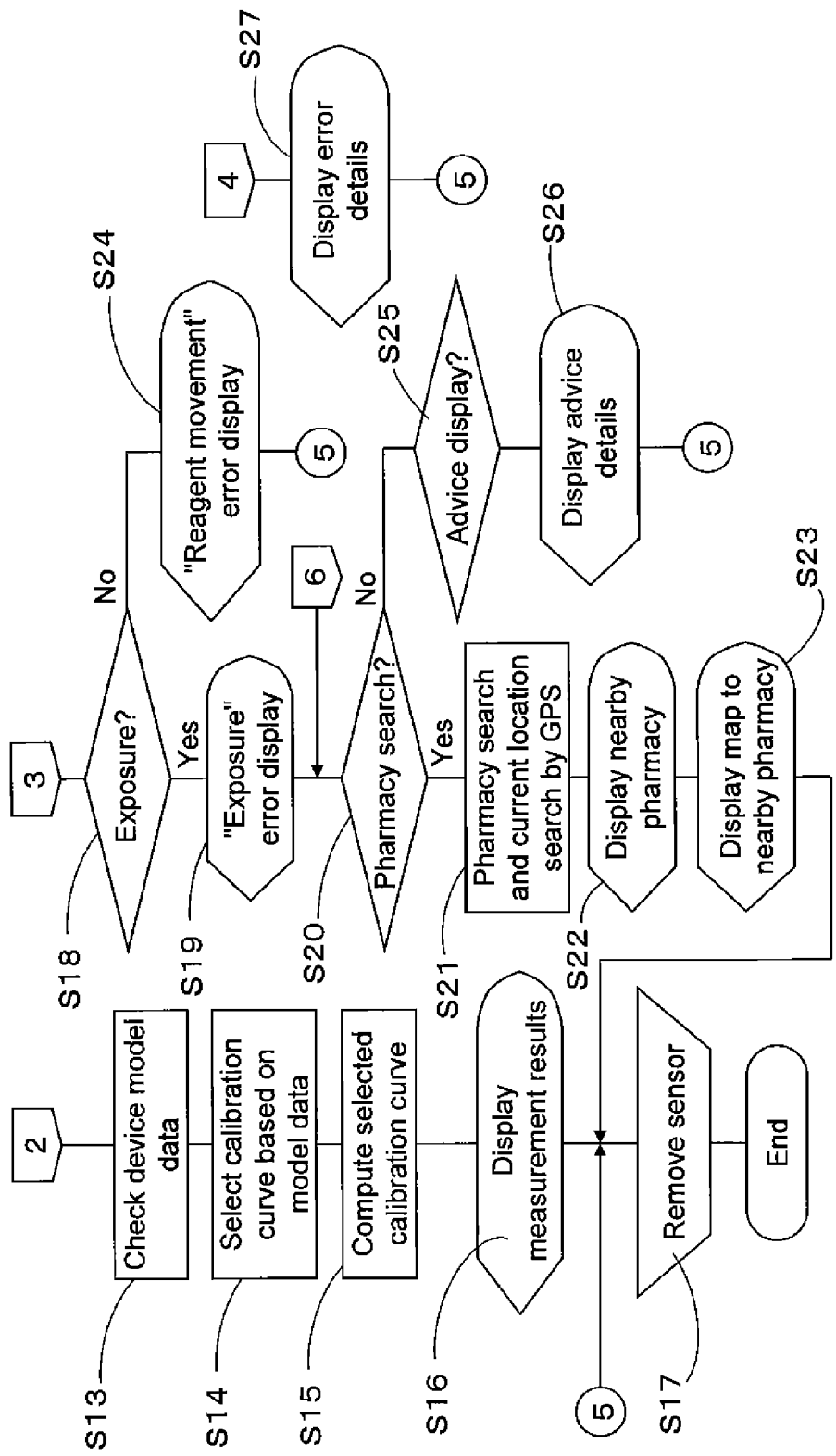
FIG. 9 is an operating flowchart of the biological sample measuring device in this embodiment.

If no error of any kind is detected, the device model data is checked (S13 in FIG. 9), a calibration curve is selected (S14 in FIG. 9), and the measurement value for the biological sample found from the selected calibration curve is computed (S15 in FIG. 9). The measurement results (measurement values, etc.) are then displayed on the display section 2 (S16 in FIG. 9). After this, the biological sample measurement sensor 3 is taken out of the sensor insertion opening 4, which completes the measurement (S17 in FIG. 9).

On the other hand, if it is determined that an abnormal waveform error has occurred, the type of error that has occurred is identified using the above method for identifying an exposure error, in order to identify the type of error more precisely (S18 in FIG. 9).

If it is determined that an exposure error has occurred, the details thereof are displayed on the display section 2 (S19 in FIG. 9).

FIGS. 12a and 12b show examples of the display when an exposure error has occurred.

FIG. 12a shows a segment display example that merely tells the user that an error has occurred. More specifically, the error code "E7," which indicates the occurrence of an exposure error, is displayed. FIG. 12b is an example of the display when a dot matrix is used, which not only indicates an error, but also gives a help display, such as "advice" to the user or a "pharmacy search."

This help display is provided because if the occurrence of an exposure error is detected, it is possible that the remaining biological sample measurement sensors 3 had by the user have also become similarly defective. Thus, if it should become urgently necessary for new biological sample measurement sensors 3 to be procured, the user can select "pharmacy search" (S20 in FIG. 9) to make use of the position detector 8 (GPS function) built into the main body case 1 and thereby recognize the current location and find the closest pharmacy by accessing an external pharmacy database with the communication section 22 (S22 in FIG. 9). If map data is available at this point, a map to the pharmacy can also be displayed on the display section 2 (S23 in FIG. 9). FIG. 12d shows an example of this display.

After this, the biological sample measurement sensor 3 is taken out of the sensor insertion opening 4, and measurement is ended. If measurement is to be performed again, the flow returns to S1 in FIG. 8, and the procedure can be restarted by putting another biological sample measurement sensor 3 into the sensor insertion opening 4. The map data to pharmacies, etc., is stored in a pharmacy data memory 23 (FIG. 2). Also, as shown in FIG. 2, this biological sample measuring device is provided with a power supply unit 7 that supplies power to the various components.

If advice display is selected (S25 in FIG. 9), then instructions for storing the biological sample measurement sensors 3 and warnings are displayed on the display section 2 (S26 in FIG. 9).

Other than when it has been determined that an exposure error has occurred, it is determined that a reagent movement error has occurred, and details thereof are displayed on the display section 2 (S24 in FIG. 9).

FIGS. 13a, 13b, and 13c show examples of what is displayed on the display section 2 when it has been determined that a reagent movement error has occurred.

FIG. 13a is when a segment display is given on the display section 2, and show the error code "E9," which corresponds to a reagent movement error. FIG. 13b is when a dot matrix display is given on the display section 2, and shows directly that a reagent movement error has occurred. FIG. 13c shows advice in that case, such as warnings.

Next, the detailed flow of error detection when an exposure error or a reagent movement error has occurred will be described through reference to FIG. 10.

Figure 10:
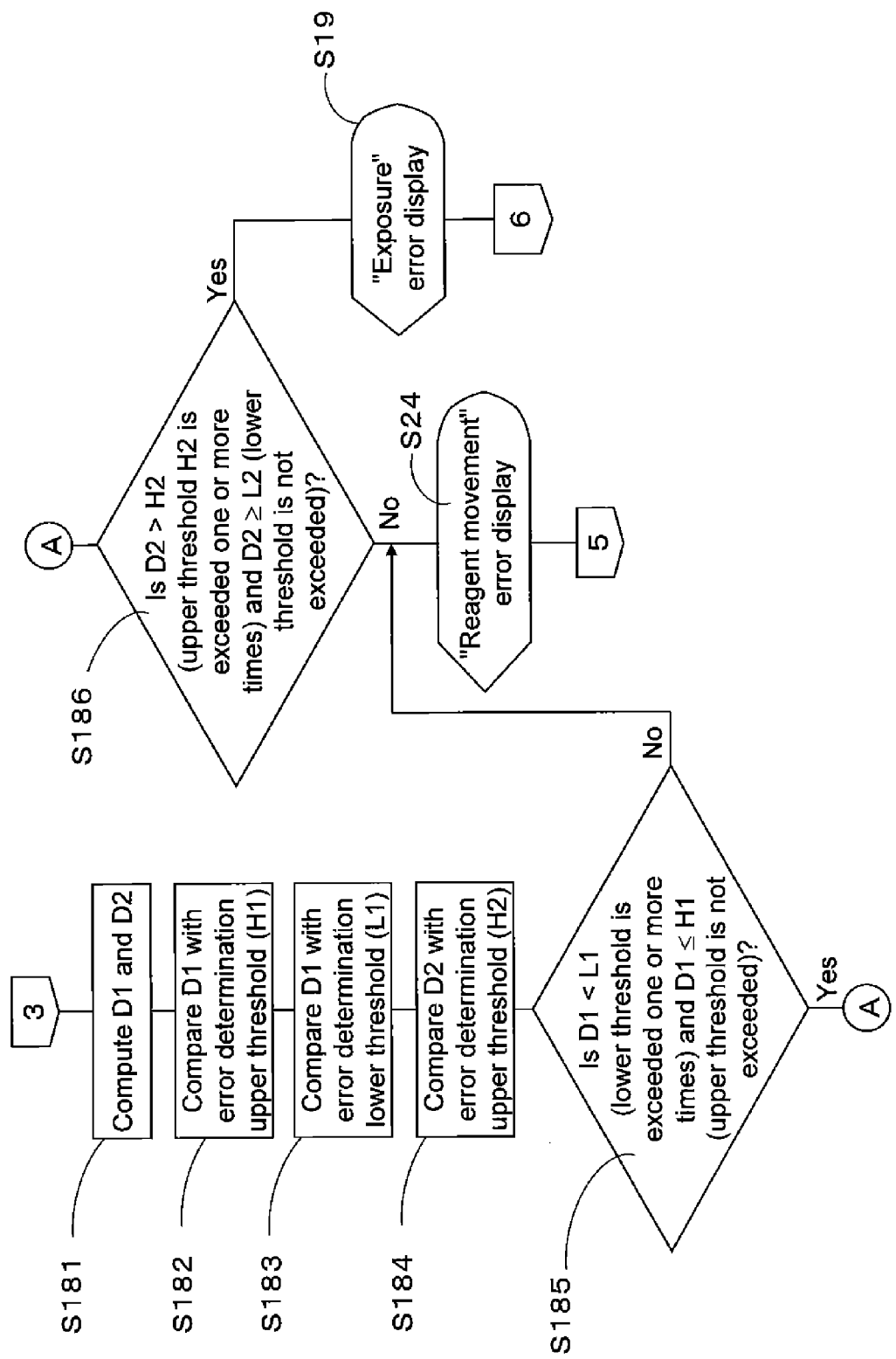
FIG. 10 is an operating flowchart of the biological sample measuring device in this embodiment.

The flow in FIG. 10 shows the details of what is carried out in the steps of determining the occurrence of an exposure error as shown in FIG. 9 (S18 in FIG. 9) and the display thereof (S19 in FIG. 9), and displaying the occurrence of a reagent movement error (S24 in FIG. 9), when it has been determined that there is an abnormal waveform error in the flow shown in FIG. 8 (S11 in FIG. 8).

First, the first and second abnormal determination values D1(t1) and D1(t2) are computed on the basis of the first and second measurement values m1 and m2 in the first measurement period at the first application time T1, and the third and fourth measurement values m3 and m4 in the second measurement period at the second application time T2. Also, the third abnormal determination value D2(t3) is computed on the basis of the first and second abnormal determination values (S181 in FIG. 10).

Next, the above-mentioned first and second abnormal determination values D1(t1) and D1(t2) are compared with the upper threshold H1 used for determination of D1 (S182 in FIG. 10).

Similarly, the first and second abnormal determination values D1(t1) and D1(t2) are compared with the lower threshold L1 used for determination of D1 (S183 in FIG. 10). Also, the above-mentioned third abnormal determination value D2(t3) is compared with the upper threshold H2 used for determination of D2 (S184 in FIG. 10).

As shown in FIGS. 6a, 6b, and 6c, these are functions of time variables t1, t2, and t3, and are data about specific time ranges (in the above example, t1, t2, and t3 are 3.6 to 5 sec), so the first, second, and third abnormal determination values D1(t1), D1(t2), and D2(t3) each constitute a data group (a grouping of a plurality of sets of data). All of the data in these data groups are compared with the upper threshold H1 and lower threshold L1 for the above-mentioned D1, and with the upper threshold H2 and the lower threshold L2 for the above-mentioned D2.

From the above comparisons, first a determination as to whether a detected abnormal waveform is one caused by exposure error is performed by the following procedure.

First, it is determined whether or not the first and second abnormal determination values D1(t1) and D1(t2) are under the lower threshold L1 for D1 (actually, whether the number of times they are under L1 is one or more), and the first and second abnormal determination values D1(t1) and D1(t2) do not exceed the upper threshold H1 for D1 (actually, whether the number of times they exceed H1 is zero) (S185 in FIG. 10).

If the above conditions are met, the flow moves to S186 in FIG. 10. Here, it is determined whether or not the third abnormal determination value D2(t3) exceeds the upper threshold H2 for D2 (whether the number of times it exceeds H2 is one or more), and the third abnormal determination value D2(t3) is not under the lower threshold L2 for D2 (whether the number of times it is under L2 is zero). If these conditions are met, it is determined that an exposure error has occurred, and a corresponding display is given (S19 in FIG. 9).

On the other hand, if the above conditions are not met, it is concluded that a reagent movement error has occurred, and a corresponding display is given (S24 in FIG. 9).

FIG. 11 is a table in which the above-mentioned determination conditions are arranged in a matrix. The vertical axis in FIG. 11 is the first and second abnormal determination values D1(t1) and D1(t2), and the horizontal axis is the third abnormal determination value D2(t3).

The vertical axis D1(t) in the table refers collectively to the first and second abnormal determination values D1(t1) and D1(t2), and the conditions thereof are given below, starting from the top.

(1) <L1: the number of times D1 is under the lower threshold L1 is at least one, and >H1: the number of times D1 exceeds the upper threshold H1 is at least one.

(2) <L1: the number of times D1 is under the lower threshold L1 is at least one, and ≤H1: the number of times D1 exceeds the upper threshold H1 is zero (does not happen).

(3) ≥L1: the number of times D1 is under the lower threshold L1 is zero (does not happen), and >H1: the number of times D1 exceeds the upper threshold H1 is at least one.

(4) ≥L1: the number of times D1 is under the lower threshold L1 is zero (does not happen), and ≤H1: the number of times D1 exceeds the upper threshold H1 is zero (does not happen).

Similarly, the horizontal axis D2(t) in the table is the third abnormal determination value D2(t3), and the conditions thereof are given below, starting from the left.

(5) <L2: the number of times D2 is under the lower threshold L2 is at least one, and
>H2: the number of times D2 exceeds the upper threshold H2 is at least one.

(6) <L2: the number of times D2 is under the lower threshold L2 is at least one, and
≤H2: the number of times D2 exceeds the upper threshold H2 is zero (does not happen).

(7) ≥L2: the number of times D2 is under the lower threshold L2 is zero (does not happen), and
>H2: the number of times D2 exceeds the upper threshold H2 is at least one.

(8) ≥L2: the number of times D2 is under the lower threshold L2 is zero (does not happen), and
≤H2: the number of times D2 exceeds the upper threshold H2 is zero (does not happen).

As discussed above, with the biological sample measuring device of this embodiment, the occurrence of an exposure error and the occurrence of a reagent movement error can be identified by combining conditions (1) to (4) on the vertical axis and conditions (5) to (8) on the horizontal axis.

As can be seen from the conditions given in FIG. 11, when condition (4) on the vertical axis is met, and condition (8) on the horizontal axis is met, this means that the biological sample measurement sensor 3 is normal. Thus, the measurement value produced by the biological sample measuring device at this point is displayed on the display section 2.

When condition (2) on the vertical axis is met, and conditions (7) and (8) on the horizontal axis are met, this means that an exposure error (E7) has occurred. Otherwise, it means that a reagent movement error (E9) has occurred.

In the example described in this embodiment, the error code corresponding to an exposure error was "E7," and the error code corresponding to a reagent movement error was "E9," but the present invention is not limited to this.

Also, other errors besides the above-mentioned abnormal waveform error that can be detected by a biological sample measuring device include a front/back inverted insertion error when the insertion direction of the biological sample measurement sensor 3 is backward, a used sensor error when a used biological sample measurement sensor is re-inserted, an improper temperature error when the temperature data exceeds the measurement compensation range, and so forth.

With the biological sample measuring device in this embodiment, as discussed above, a measurement result obtained using a biological sample measurement sensor 3 that has been left out in a place of high humidity for an extended period can be determined to indicate the occurrence of an exposure error, or an improper measurement caused by impact or the like exerted from the outside during measurement can be determined to indicate that a reagent movement error has occurred, on the basis of the first, second, and third abnormal determination values D1(t1), D1(t2), and D2(t3). As a result, just those measurement results obtained by proper measurement can be displayed on the display section 2, and erroneous measurement results based on an abnormal waveform will not be accidentally recognized by the user as correct measurement results.

Furthermore, with the biological sample measuring device in this embodiment, the type of error (exposure error or reagent movement error) can also be determined from the measurement result based on an abnormal waveform. As a result, the user can be notified of the type of error and given advice about countermeasures, etc., so that the user can subsequently take appropriate action.

Threshold Variation/Switching Control

As discussed above, with the biological sample measuring device in this embodiment, error identification is performed using the determination-use first lower threshold L1, first upper threshold H1, second lower threshold L2, and second upper threshold H2.

We will now describe the processing in which error identification is performed while varying/switching these thresholds on the basis of specific conditions.

The need for varying/switching the above thresholds will now be examined.

More specifically, the response value (input signal level) obtained during measurement with the biological sample measuring device tends to vary greatly depending on the concentration of the glucose or other substance being measured, the ambient temperature during measurement, the Hct value (red blood cell ratio), and so forth.

For example, if the glucose concentration is high, the response value (response current) tends to be larger, and conversely, if the concentration is low, the response value tends to be smaller.

Similarly, when the ambient temperature during measurement is high, the response value tends to be larger, and conversely, when the ambient temperature is low, the response value tends to be smaller.

Further, when the Hct value is high, the response value tends to be smaller, and conversely, when the Hct value is low, the response value tends to be larger.

In view of this, with the biological sample measuring device in this embodiment, the determination section 19 can vary/switch the level of each threshold according to the level of the information, such as the concentration of the substance being measured, the ambient temperature during measurement, or the Hct value, at a timing that is prior to when the above-mentioned error identification is carried out.

This varying/switching of the various thresholds may be carried out using the concentration of the substance being measured, the ambient temperature, and the Hct value as single conditions for varying/switching the thresholds, or these may be combined.

Figure 15C:
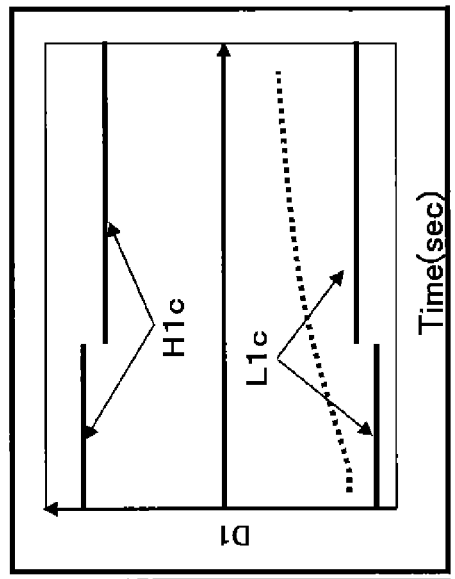
FIGS. 15a, 15b, and 15c are graphs of the changes in the first difference determination value under conditions in which the reaction proceeds slowly during normal measurement, under normal conditions, and under conditions in which the reaction proceeds readily.
Figure 15B:
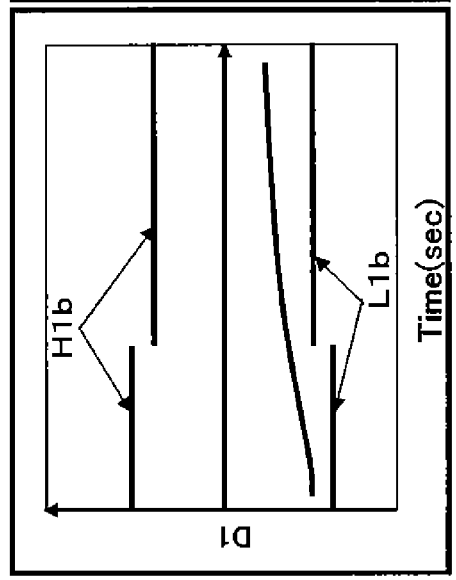
Figure 15A:
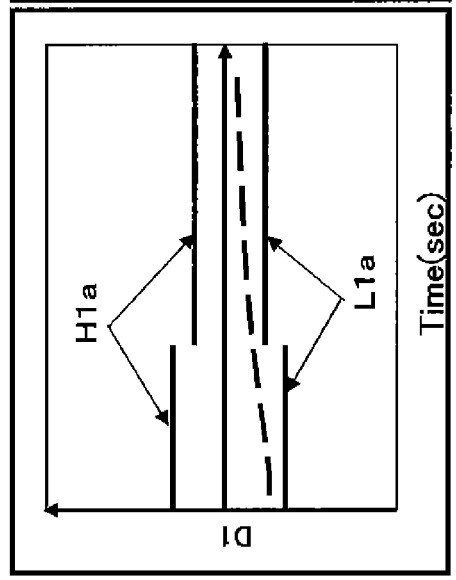

More specifically, as shown in FIGS. 15a to 15c, a comparison of a case in which the reaction between the sample and the reagent does not readily proceed during measurement (low glucose concentration, high ambient temperature, high Hct value, etc.), a case in which the reaction is standard (medium glucose concentration, high ambient temperature, medium Hct value), and a case in which the reaction proceeds readily (high glucose concentration, high ambient temperature, low Hct value) may reveal that there is a difference between the detection level and the input signal of 10 times or more. As a result, the first difference determination value, etc., will end up varying greatly between the waveform shown in FIG. 15a and the waveform shown in FIG. 15c, depending on the magnitude of this difference, so there is the risk that it will be difficult to perform error determination accurately.

With the biological sample measuring device in this embodiment, in light of the above, a method is employed in which a plurality of thresholds are preset, and the values of these thresholds can be varied/switched on the basis of the above-mentioned information about the concentration of the substance being measured, the ambient temperature during measurement, and the Hct value (either singly or in combinations).

Specifically, in the three examples shown in FIGS. 15a to 15c, upper thresholds H1a, H1b, and H1c of two stages each, and lower thresholds L1a, L1b, and L1c of two stages each are set for D1, which is a first difference determination value. Thus, error determination is performed using a total of six kinds of threshold (H1a, H1b, H1c, L1a, L1b, and L1c) according to the specific conditions, such as the concentration of the substance being measured.

Having two stages of upper threshold and lower threshold is the same as what is shown in the above-mentioned FIGS. 6b and 7b.

That is, with the determination in FIG. 6b or 7b, three each of a first upper threshold and a first lower threshold are prepared, and more accurate error determination can be performed by switching the three thresholds according to the concentration of the glucose or other such substance being measured, the ambient temperature, the Hct value, etc.

The description here was for the first difference determination value D1, but the same applies to the second difference determination value D2 as shown in FIGS. 6c and 7c.

Specifically, a total of six kinds of threshold, namely, the upper thresholds H2a, H2b, and H2c of two stages each, and the lower thresholds L2a, L2b, and L2c of two stages each are set for D2, which is a second difference determination value, which allows error determination to be performed according to the specific conditions, such as the concentration of the substance being measured.

Consequently, since the resulting response current varies with the concentration of the substance being measured, the ambient temperature, the Hct value, and so forth, if a plurality of error determination-use thresholds are set according to the level of various conditions (such as the glucose concentration, the ambient temperature, and the Hct value), when more accurate error determination can be performed, without being affected by the level of the concentration of the substance being measured, the ambient temperature during measurement, or the Hct value.

As another control in which various thresholds are varied/switched, a method may be employed in which thresholds (error determination-use upper thresholds and lower thresholds, etc.) can be varied/switched according to the ratio between the above-mentioned information about the concentration of the substance being measured, the ambient temperature during measurement, and the Hct value, and preset reference values (such as a temperature of 25° C. and an Hct value 45%).

Here again, just as discussed above, error determination can be performed accurately without being affected by the level of the concentration of the substance being measured, the ambient temperature during measurement, or the Hct value.

In the above description, an example was given of determining between an exposure error and a reagent movement error, but this threshold varying/switching control is not limited to just these two kinds of error identification.

That is, with the biological sample measuring device in this embodiment, it is possible to improve accuracy in the identification of all other kinds of waveform error that caused by abnormal waveforms.

Embodiment 2

The biological sample measuring device pertaining to another embodiment of the present invention will be described through reference to FIGS. 14a and 14b.

Specifically, FIGS. 14a and 14b are oblique views of the configuration of the biological sample measuring device in this embodiment.

The biological sample measuring device in this embodiment comprises an interchangeable panel 53.

FIG. 14a shows the state when the panel 53 has been mounted to a main body case 51, while FIG. 14b shows the state when the panel 53 has been removed from the main body case 51.

As shown in FIGS. 14a and 14b, a sensor insertion opening 54 of a biological sample measurement sensor 3 (not shown) is provided at one end of the main body case 51.

Also, a display section 52 and a control dial 55 are provided to the front of the main body case 51. The dial 55 also allows push operation, so after the dial 55 is turned to select a category on the screen menu displayed on the display section 52, the dial 55 can be pushed to enter the selection of this menu category.

A shuttle dial is shown in FIGS. 14a and 14b, but a jog dial may be used instead. Also, a push operation may also be used, of course, when switching the power on and off to the main body case 51.

The biological sample measuring device in this embodiment has an external memory (not shown) such as an SD memory in the panel 53. The SD memory holds pharmacy data by locale (such as pharmacy names, addresses, and contact person). Thus, when the panel 53 is mounted to the main body case 51, the SD memory installed in the panel 53 is electrically connected to the electrical circuit inside the main body case 51 via connectors 56 and 57 (just one connector may be used) provided to the main body case 51. As a result, when an exposure error occurs, the pharmacy data stored in the SD memory can be displayed on the display section 52.

The position detector (GPS function) or communication section (communication function) installed in the main body case 1 described in Embodiment 1 above may also be installed in the panel 53.

Consequently, the main body case 51 can have a common, simple configuration, and many different kinds of optional functions can be added or modified by exchanging the panel 53. This makes it possible to better enhance user support to meet the needs of the user.

Other Embodiments

Embodiments of the present invention were described above, but the present invention is not limited to or by these embodiments, and various modifications are possible without departing from the gist of the invention.

(A)

In Embodiment 1 above, an example was given in which the upper and lower thresholds were set in two stages consisting of the first and second halves of the measurement time, but the present invention is not limited to this.

For example, as shown in the graphs in FIGS. 16a to 16c, the horizontal axis indicating measurement time may be divided in three, and different upper and lower thresholds may be set in three stages in each time period.

FIG. 16a shows the first difference determination value D1 when the reaction between the sample and the reagent does not proceed readily during measurement (low glucose concentration, high ambient temperature, high Hct value, etc.). In this case, the upper threshold of D1 is provided in three stages (H1-1a, H1-2a, and H1-3a), and the lower threshold in three stages (L1-1a, L1-2a, and L1-3a).

Similarly, FIG. 16b shows the first difference determination value D1 when the reaction is standard (medium glucose concentration, high ambient temperature, medium Hct value). In this case, the upper threshold of D1 is provided in three stages (H1-1b, H1-2b, and H1-3b), and the lower threshold in three stages (L1-1b, L1-2b, and L1-3b).

FIG. 16c shows the first difference determination value D1 when the reaction proceeds readily (high glucose concentration, high ambient temperature, low Hct value). In this case, the upper threshold of D1 is provided in three stages (H1-1c, H1-2c, and H1-3c), and the lower threshold in three stages (L1-1c, L1-2c, and L1-3c).

Specifically, as shown in FIGS. 16a to 16c, a comparison between a case in which the reaction between the sample and the reagent does not proceed readily during measurement, a case in which the reaction is standard, and a case in which the reaction proceeds readily reveals that there is a large difference in the measurement values between the first and second halves of the measurement time, particularly when the reaction does not proceed readily. Thus, in order to absorb these differences and carry out more accurate error determination, it is preferable for the thresholds to be set in a plurality of (three or more) stages.

Thus, statistically obtained error determination thresholds can be seen to vary with the measurement time, so accuracy in error determination can be further improved by dividing the appropriate thresholds up into a plurality of stages according to measurement time.

The first difference determination value D1 was described here, but the same applies to the second difference determination value D2.

That is, for the second difference determination value D2 when the reaction between the sample and the reagent does not proceed readily during measurement, the upper threshold of D2 may be provided in three stages of H2-1a, H2-2a, and H2-3a, and the lower threshold in three stages of L2-1a, L2-2a, and L2-3a. Similarly, for the second difference determination value D2 with a standard reaction, the upper threshold of D2 may be provided in three stages of H2-1b, H2-2b, and H2-3b, and the lower threshold in three stages of L2-1b, L2-2b, and L2-3b. Furthermore, for the second difference determination value D2 when the reaction proceeds readily, the upper threshold of D2 may be provided in three stages of H2-1c, H2-2c, and H2-3c, and the lower threshold in three stages of L2-1c, L2-2c, and L2-3c.

This allows the accuracy of error determination to be further improved, just as with the first difference determination value D1.

In the above description, an example was given of identifying an exposure error or a reagent movement error, but this varying/switching control of the thresholds is not limited to just these two kinds of error identification.

That is, with the biological sample measuring device of the present invention, accuracy can be improved in the identification of all other types of waveform error caused by abnormal waveforms.

(B)

In Embodiment 1 above, an example was given in which a pause time in which no voltage was applied was provided between the first application time and the second application time, but the present invention is not limited to this.

Figure 17A:
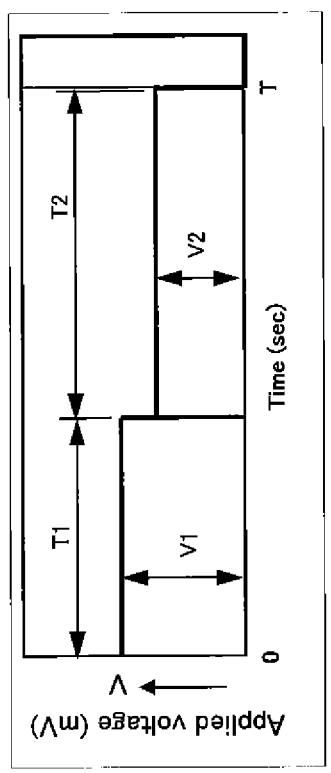
FIG. 17a is a graph of the voltage application pattern when no pause is provided between the first and second application periods with the biological sample measuring device pertaining to yet another embodiment of the present invention.

For example, as shown in FIG. 17a, error identification, etc., may be performed with a voltage application pattern in which no pause is provided between the first application time and the second application time.

Figure 17B:
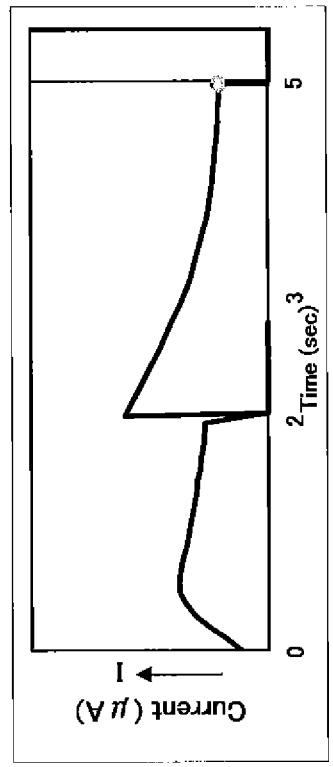
FIG. 17b is a graph of the waveform of the measurement input signal at this point.

Here again, as shown in FIG. 17b, just as in Embodiment 1 above, error determination can be performed by detecting the waveform of the measurement signal (input signal).

If voltage is applied two or more times, the same error determination is possible by combining various application waveforms (voltage and number of applications). In this case, it is preferable to use the optimal voltage application pattern and error determination method according to the targeted error determination (such as exposure error, or a reagent movement error caused by impact or the like during measurement).

(C)

In Embodiment 1 above and another embodiment (B), an example was given in which the voltage applied in the first application time was set to be greater than the voltage applied in the second application time, but the present invention is not limited to this.

Figure 18A:
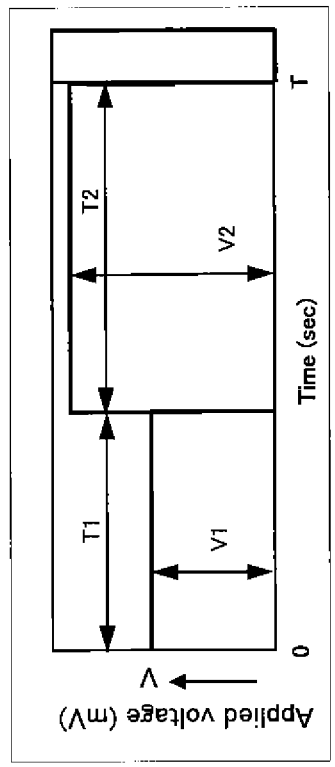
FIG. 18a is a graph of the voltage application pattern when the amounts of voltage applied are reversed between the first and second application periods with the biological sample measuring device in FIG. 17.

For example, as shown in FIG. 18a, just as in the other embodiment (B) above, if no pause time is provided between the first application time and the second application time, the voltage applied in the first application time may be set to be less than the voltage applied in the second application time.

Figure 18B:
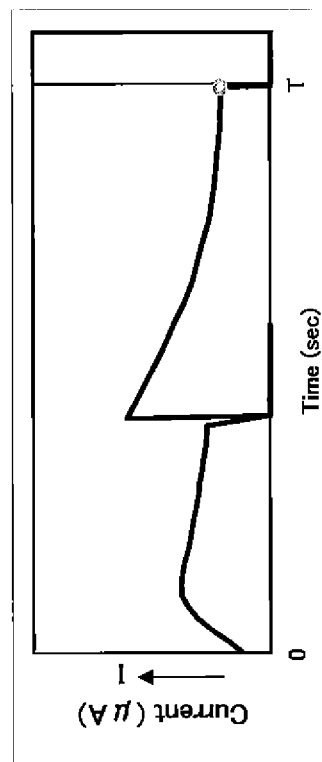
FIG. 18b is a graph of the waveform of the measurement input signal at this point.

In this case, as shown in FIG. 18b, error determination can be performed by detecting the waveform of the measurement signal (input signal) for each application time.

INDUSTRIAL APPLICABILITY

The biological sample measuring device of the present invention has the effect of allowing the user to appropriately deal with the situation after an error has been detected, by precisely identifying the type of error. Therefore, this device is expected to find use as a biological sample measuring device that detects biological information such as blood glucose levels.

REFERENCE SIGNS LIST 1 main body case
2 display section
3 biological sample measurement sensor
4 sensor mounting section
5, 6 control button
7 power supply unit
8 position detector (equipped with GPS function)
11 sensor insertion detector
12 voltage applicator
13 current-voltage converter
14, 15 amplifier
16, 17 switch
18 analog/digital converter
19 determination section
19a calculating unit
20 controller
21 memory
22 communication section
23 pharmacy data memory
40 sensor canister
51 main body case
52 display section
53 panel
54 sensor insertion opening
55 dial
56, 57 connector

The invention claimed is:
1. A biological sample measuring device, comprising:
a sensor mounting section to which a biological sample measurement sensor is mounted, wherein a reagent is to be placed on the biological sample measurement sensor;
a main body case having the sensor mounting section;

a measurement section that is connected to the sensor mounting section;

a controller that is connected to the measurement section; and a determination section, a calculating unit, and a display section that are connected to the controller; and a memory section that stores a first upper threshold, a first lower threshold, a second upper threshold, and a second lower threshold, the memory section is connected to the determination section;

wherein the measurement section is programmed to measure current values at intervals in a first measurement period, and is programmed to measure at intervals in a second measurement period that comes after the first measurement period, and the calculating unit is programmed to:

calculate a plurality of first difference determination values by subtracting the current values measured at the intervals in the first measurement period from a plurality of current values measured at the intervals in the second measurement period, respectively, and calculate a second difference determination value by subtracting one of the first difference determination values from another of the first difference determination values; and the determining section is programmed to:

compare the plurality of first difference determination values with both the first upper threshold and the first lower threshold to determine a first comparison result, compare the second difference determination value with both the second upper threshold and the second lower threshold to determine a second comparison result, and determine that an error exists if the first comparison result fails to satisfy a first condition and the second comparison result fails to satisfy a second condition, and if an error is determined to exist, determine that the error is an exposure error if the first comparison result satisfies a third condition and the second comparison result satisfies a fourth condition, and determine that the error is a reagent movement error if the error is not determined to be an exposure error.

2. The biological sample measuring device according to claim 1, wherein the determination section finds first and second measurement values obtained at specific intervals in the first measurement period, and finds third and fourth measurement values obtained at specific intervals in the second measurement period, and the difference obtained by subtracting the first measurement value from the third measurement value, and the difference obtained by subtracting the second measurement value from the fourth measurement value are used as the plurality of first difference determination values.

3. The biological sample measuring device according to claim 1, wherein the absolute value of the second lower threshold is less than the absolute value of the first upper threshold and the first lower threshold.

4. The biological sample measuring device according to claim 1, wherein it is determined that a reagent movement error of the biological sample measurement sensor has occurred if none of the plurality of first difference determination values or the second difference determination value satisfies the following conditions (1) and (2):

(1) at least one of the plurality of first difference determination values is less than the first lower threshold, and at least one of the plurality of first difference determination values is at or under the first upper threshold, and at least one of the second difference determination values is at or over the second lower threshold, (2) the plurality of first difference determination values are at or above the first lower threshold and at or below the first upper threshold, and the second difference determination value is at or above the second lower threshold and at or below the second upper threshold.

5. The biological sample measuring device according to claim 4, wherein the absolute values of the second upper threshold and the second lower threshold are less than the absolute values of the first upper threshold and the first lower threshold.

6. The biological sample measuring device according to claim 1, wherein the controller displays the occurrence of an error on the display section when it is determined by the determination section that the exposure error or the reagent movement error has occurred.

7. The biological sample measuring device according to claim 6, wherein the controller displays information about what to do after the occurrence of the exposure error or the reagent movement error on the display section.

8. The biological sample measuring device according to claim 1, wherein the measurement involves measuring the oxidation or reduction current value between a working electrode and a counter electrode provided to the biological sample measurement sensor.

9. The biological sample measuring device according to claim 1, wherein the determination section switches the first threshold and/or the second threshold.

10. The biological sample measuring device according to claim 9, wherein the determination section switches at least one of the first threshold and/or second threshold according to the concentration of a specimen, the ambient temperature during measurement, or the Hct value.

* * * * *